United States Patent
Hall et al.

(10) Patent No.: US 10,882,884 B2
(45) Date of Patent: Jan. 5, 2021

(54) STEREOSELECTIVE SYNTHESIS OF PHOSPHOROTHIOATE OLIGORIBONUCLEOTIDES

(71) Applicant: ETH ZURICH, Zurich (CH)

(72) Inventors: Jonathan Hall, Dornach (CH); Meiling Li, Rheinfelden (CH)

(73) Assignee: ETH ZURICH, Zurich (CH)

( * ) Notice: Subject to any disclaimer, the term of this patent is extended or adjusted under 35 U.S.C. 154(b) by 0 days.

(21) Appl. No.: 16/302,091

(22) PCT Filed: May 18, 2017

(86) PCT No.: PCT/EP2017/061991
§ 371 (c)(1),
(2) Date: Nov. 15, 2018

(87) PCT Pub. No.: WO2017/198775
PCT Pub. Date: Nov. 23, 2017

(65) Prior Publication Data
US 2019/0135849 A1   May 9, 2019

(30) Foreign Application Priority Data

May 18, 2016  (EP) ..................................... 16170102
Sep. 19, 2016  (EP) ..................................... 16189480

(51) Int. Cl.
| C07H 19/06 | (2006.01) |
| C07H 19/16 | (2006.01) |
| C07H 21/00 | (2006.01) |
| C07H 21/02 | (2006.01) |

(52) U.S. Cl.
CPC ............. *C07H 19/06* (2013.01); *C07H 19/16* (2013.01); *C07H 21/00* (2013.01); *C07H 21/02* (2013.01)

(58) Field of Classification Search
None
See application file for complete search history.

(56) References Cited

FOREIGN PATENT DOCUMENTS

| WO | WO 2005/014609 A2 | 2/2005 |
| WO | WO 2010/064146 A2 | 6/2010 |
| WO | WO 2012/039448 A1 | 3/2012 |
| WO | WO 2014/010250 A1 | 1/2014 |
| WO | WO 2014/012081 A2 | 1/2014 |
| WO | WO-2014012081 A2 * | 1/2014 ........... C12N 15/113 |

OTHER PUBLICATIONS

Wan et al., Nucleic Acids Research, 2014, vol. 42, No. 22, pp. 13456-13468 (Year: 2014).*
International Search Report issued in PCT/EP2017/061991, dated Jul. 11, 2017.
Geary et al., "Pharmacokinetic Properties of 2'-O-(2-Methoxyethyl)-Modified Oligonucleotide Analogs in Rats," *J Pharmacol Exp Ther* 296(3):890-897 (2001).
Nukaga et al., "Stereocontrolled Solid-Phase Synthesis of Phosphorothioate Oligoribonucleotides Using 2'-O-(2-Cyanoethoxymethyl)-nucleoside 3'-O-Oxazaphospholidine Monomers," *J Org Chem* 77(18):7913-7922 (2012).
Oka et al., "Solid-Phase Synthesis of Stereoregular Oligodeoxyribonucleoside Phosphorothioates Using Bicyclic Oxazaphospholidine Derivatives as Monomer Units," *J Am Soc Chem* 130(47):16031-16037 (2008).
Oka et al., "Stereocontrolled Synthesis of Oligoribonucleoside Phosphorothioates by an Oxazaphospholidine Approach," *Org Lett* 11(4):967-970 (2009).
Wan et al., "Synthesis, biophysical properties and biological activity of second generation antisense oligonucleotides containing chiral phosphorothioate linkages," *Nucleic Acids Res* 42(22):13456-13468 (2014).
Beaucage and Iyer, "The Synthesis of Modified Oligonucleotides by the Phosphoramidite Approach and Their Applications," *Tetrahedron* 49(2*:6123-6194 (1993).
Jarvis, "Could Stereopurity Reinvigorate the Antisense Field?" *C&EN* 94(26): 20-21 (2016).

(Continued)

*Primary Examiner* — Traviss C McIntosh, III
(74) *Attorney, Agent, or Firm* — Medler Ferro Woodhouse & Mills PLLC

(57) ABSTRACT

The present invention relates to chiral phosphoramidites represented by formula (Ia) or formula (Ib)

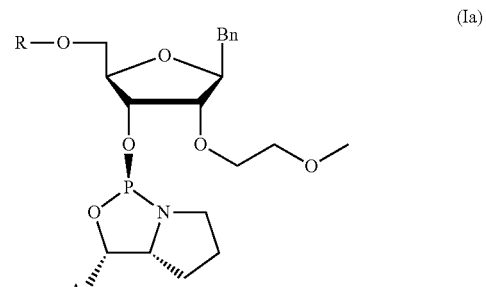

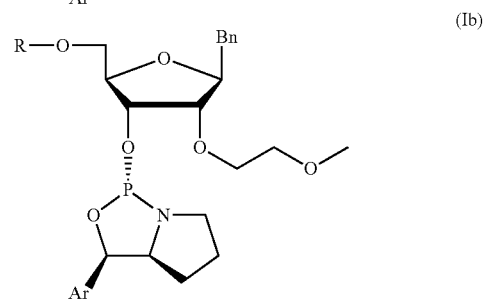

as novel monomers for the synthesis of stereodefined phosphorothioate MOE oligonucleotides. Furthermore, the present invention relates to a method for synthesizing stereodefined phosphorothioate MOE oligonucleotides using said novel chiral phosphoramidites.

30 Claims, No Drawings
Specification includes a Sequence Listing.

(56) References Cited

OTHER PUBLICATIONS

Oka et al., "An Oxazaphospholidine Approach for the Stereocontrolled Synthesis of Oligonucleoside Phosphorothioates," *JACS* 125: 8307-8317 (2003).
Guidebook for the Synthesis of Oligonucleotides Product Guide 2015/16 Version 1.2 (Mar. 16, 2015) published by Link Technologies Ltd.

* cited by examiner

SEQUENCE LISTING

```
<160> NUMBER OF SEQ ID NOS: 2

<210> SEQ ID NO 1
<211> LENGTH: 12
<212> TYPE: RNA
<213> ORGANISM: artificial sequence
<220> FEATURE:
<223> OTHER INFORMATION: All-(Rp)-PS-MOE
<220> FEATURE:
<221> NAME/KEY: modified_base
<222> LOCATION: (1)..(1)
<223> OTHER INFORMATION: t
<220> FEATURE:
<221> NAME/KEY: misc_feature
<222> LOCATION: (1)..(12)
<223> OTHER INFORMATION: all phosphorthioates
<220> FEATURE:
<221> NAME/KEY: misc_feature
<222> LOCATION: (1)..(12)
<223> OTHER INFORMATION: all Rp
<220> FEATURE:
<221> NAME/KEY: modified_base
<222> LOCATION: (4)..(4)
<223> OTHER INFORMATION: m5c
<220> FEATURE:
<221> NAME/KEY: modified_base
<222> LOCATION: (7)..(8)
<223> OTHER INFORMATION: m5c
<220> FEATURE:
<221> NAME/KEY: modified_base
<222> LOCATION: (9)..(9)
<223> OTHER INFORMATION: t

<400> SEQUENCE: 1
uagcagccug ag                                                          12

<210> SEQ ID NO 2
<211> LENGTH: 12
<212> TYPE: RNA
<213> ORGANISM: artificial sequence
<220> FEATURE:
<223> OTHER INFORMATION: All-(Sp)-PS MOE
<220> FEATURE:
<221> NAME/KEY: misc_feature
<222> LOCATION: (1)..(12)
<223> OTHER INFORMATION: all phosphorothioates
<220> FEATURE:
<221> NAME/KEY: misc_feature
<222> LOCATION: (1)..(12)
<223> OTHER INFORMATION: all Sp
<220> FEATURE:
<221> NAME/KEY: modified_base
<222> LOCATION: (1)..(1)
<223> OTHER INFORMATION: t
```

```
<220> FEATURE:
<221> NAME/KEY: modified_base
<222> LOCATION: (4)..(4)
<223> OTHER INFORMATION: m5c
<220> FEATURE:
<221> NAME/KEY: modified_base
<222> LOCATION: (7)..(8)
<223> OTHER INFORMATION: m5c
<220> FEATURE:
<221> NAME/KEY: modified_base
<222> LOCATION: (9)..(9)
<223> OTHER INFORMATION: m5c

<400> SEQUENCE: 2
uagcagccug ag                                                              12
```

STEREOSELECTIVE SYNTHESIS OF PHOSPHOROTHIOATE OLIGORIBONUCLEOTIDES

The present invention relates to chiral phosphoramidites represented by formula (Ia) or formula (Ib)

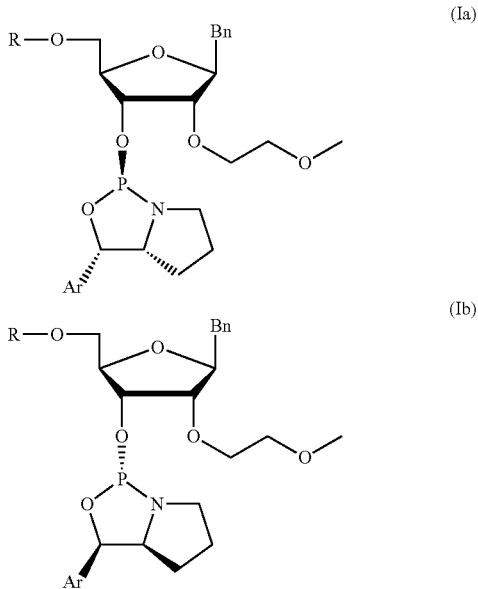

as novel monomers for the synthesis of stereodefined phosphorothioate MOE oligonucleotides. Furthermore, the present invention relates to a method for synthesizing stereodefined phosphorothioate MOE oligonucleotides using said novel chiral phosphoramidites.

RELATED ART

The use of chemically-modified antisense oligonucleotides (ASOs), as potential therapeutics has received much attention in recent years. Chemical modifications are used to enhance a number of ASO drug-like properties such as metabolic stability, RNA-affinity and bioavailability. These modifications include structural modifications of natural RNA such as 2'-OH modifications, locked nucleic acids (LNAs), peptide nucleic acids (PNAs), hexitol nucleic acids (HNAs) and many others (Deleavey G F and Damha M, Chemistry & Biology 2012, 19, 937-954). Moreover, modifications of the backbone such as the phosphorothioate (PS) linkage, where one of the non-bridging oxygen atoms of a phosphodiester linkage is replaced with a sulfur atom is one of the most widely investigated nucleic acid chemical modifications in oligonucleotide therapeutics. This PS-group is chiral at phosphorus (Rp/Sp centers) and when assembled in oligonucleotides generates a large number of diastereomers (2' diastereomers, n=number of PS-linkages), each of which possesses its own distinct physical, biochemical and biological properties. Although PS-oligonucleotides as diastereoisomeric mixtures have much improved PK (cellular uptake, nuclease stability) properties, the PK and PD (target affinity, selectivity) properties are significantly affected by the stereochemical configuration at their internucleotide linkages. Hence, a general access to stereochemically pure PS oligonucleotides would likely provide a unique opportunity to improve the PK and PD properties of this class of pharmacological agents.

A practicable solid-phase chiral synthesis of oligonucleotide phosphorothioates including oligoribonucleotide phosphorothioates (PS-ORNs), oligodesoxyribonucleotide phosphorothioates (PS-ODNs) or modified oligonucleotide phosphorothioates has thus been sought for many years but is not yet available and oligonucleotide phosphorothioates are therefore still used as diastereomeric mixtures. Moreover, only a limited number of studies on this subject have been conducted due to the unavailability of stereodefined oligonucleotide phosphorothioates and attempts to develop a method to synthesize the same with satisfying stereoselectivity have succeeded typically only in the synthesis of very short chiral oligonucleotide phosphorothioates.

Wada et al. described stereocontrolled solid-phase syntheses of PS-ORNs up to 12mers using different 2'-O-protected nucleoside 3'-O-oxazaphospholidine monomers and reported that the use of 2-cyanoethoxymethyl (CEM) groups in place of the conventional TBS groups for the 2'-O-protection of nucleoside 3'-O-oxazaphospholidine monomers improved coupling efficiency (Nukaga Y. et al., J. Org. Chem. (2012) 77:7913-7922; Oka N. et al., Org. Lett., (2009) 11(4):967-970).

Wan et al, (Nucleic Acids Res. (2014) 42:13456-13468) discloses 31 antisense oligonucleotides where the chirality of the 10-base gap region was controlled using DNA-oxazaphospholidine monomers as described by Oka (Oka et al., J. Am. Chem. Soc. (2008) 16031-16037). Based on their studies on biophysical and biological properties of the resulting ASOs it has been concluded that controlling PS chirality in the gap region of gapmers provides no significant benefits for therapeutic applications relative to the mixture of stereo-random PS ASOs. Wan et al. further refers to the added complexity and costs associated with the synthesis and characterization of chiral PS ASOs as minimizing their utility.

WO 2005/014609. WO2010/064146, WO2012/039448, WO 2014/010250, WO 2014/012081 disclose chiral auxiliaries and methods for producing stereoregular phosphorus atom-modified nucleotides using the same. However, typically the isolated yield of the monomers is low and the methods require special capping agents (N-trifluoroacetyl-imidazole) that are commercial available, but are quite expensive and highly hygroscopic. Furthermore, the isolated yields of oligonucleotide derivatives are not high, believed to be caused by the degradation reactions under the deprotection steps. This tendency becomes strongly apparent when the length of oligonucleotide derivatives becomes long.

As evident from the prior art, a major challenge to achieve stereocontrolled syntheses of oligonucleotide phosphorothioates including PS-ORNs, PS-ODNs or modified oligonucleotide phosphorothioates is the unpredictable interplay of various parameters in the synthesis. This is in particular true since the mechanisms of the key steps such as coupling and cleavage are not yet fully understood and the overall stereoselectivity and efficiency of the synthesis are highly dependent on the interaction of all components and parameters used in the course of the synthesis. In particular, the chiral phosphoramidites used as monomeric units in the interplay with the activator in the coupling step, the reagents in the sulfurization and capping step as well as with the cleavage reagents define the overall stereoselectivity and efficiency and thus, its usefulness particularly for the synthesis of longer (>15 mer) stereodefined oligonucleotide phosphorothioates (EP2620428). Beside the unpredictable interplay of various parameters in the synthesis to achieve stereocontrolled synthesis of oligonucleotide phosphorothioates, the successful solid-phase synthesis of an oligonucleotide of 20 nucleotides in length requires at least around 80 chemical reactions in linear fashion and therefore chemical conversions to be essentially quantitative in order to isolate the desired final product. This further requirement makes the development of reagents for stereocontrolled synthesis of oligonucleotide phosphorothioates including PS-ORNs, PS-ODNs or modified oligonucleotide phosphorothioates an even bigger challenge.

SUMMARY OF THE INVENTION

The present invention provides for new stereopure 2'-O-methoxyethylribose (MOE) nucleoside phosphoramidites. Moreover, the present invention provides for stereodefined PS 2'-O-methoxyethylribose (MOE) oligonucleotides by using said inventive stereopure MOE nucleoside phosphoramidites in the course of standard solid phase synthesis. As a consequence, the present invention provides for the efficient synthesis of stereodefined PS MOE oligonucleotides. Advantageously, the present invention allows to use stable and commercially available materials as starting materials to produce stereodefined phosphorothioate MOE oligonucleotides by using the inventive compounds of formula (Ia) or (Ib). Furthermore, the use of the inventive compounds of formula (Ia) or (Ib) in the course of the standard phosphoramidite syntheses avoids degradations under the de-protection steps and obviates the need of special capping agents to produce said stereodefined phosphorothioate MOE oligonucleotides.

Thus, in a first aspect, the present invention provides for a compound of formula (Ia) or formula (Ib),

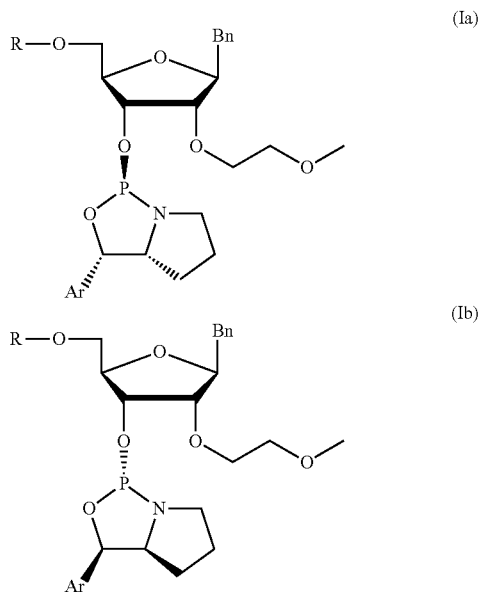

wherein Ar is phenyl (Ph, $C_6H_5$) optionally substituted with halogen, $C_1$-$C_6$alkyl, $C_3$-$C_6$cycloalkyl, $C_1$-$C_4$alkoxy; and R is a protective group of a hydroxyl group; and Bn is selected from (i) adenine, (ii) cytosine, (iii) 5-methylcytosine, (iv) guanine, (v) uracil, (vi) 5-methyluracil, or (vii) a derivative of (i), (ii), (iii), (iv), (v) or (vi). In a very preferred embodiment, Ar is phenyl. Thus, in such a very preferred embodiment, said compound of formula (Ia) is a compound of formula (IIa) and said compound of formula (Ib) is a compound of formula (IIb)

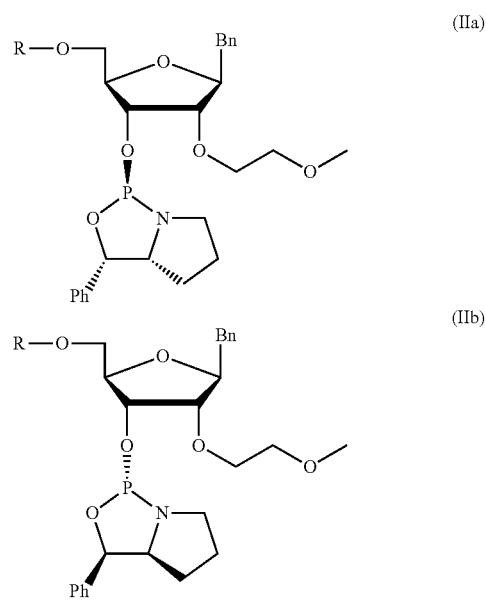

wherein R and Bn are defined as described above and herein.

Moreover, in a further aspect, the present invention provides for a method for synthesizing a stereodefined phosphorothioate MOE oligonucleotide comprising the step of coupling an inventive compound of formula (Ia) or formula (Ib) to either an oligonucleotide synthesis support or a preceding nucleotide, wherein said stereodefined phosphorothioate MOE oligonucleotide comprises at least one stereospecific phosphorothioate nucleotide pair wherein the internucleoside linkage between the nucleosides of the at least one stereospecific phosphorothioate nucleotide pair is either in the Sp configuration or in the Rp configuration, and wherein at least one of the nucleosides of the at least one stereospecific phosphorothioate nucleotide pair is a MOE nucleoside. A MOE nucleoside comprises a 2'-O-(2-methoxy)ethyl (MOE) ribose sugar modification. Thus, a MOE oligonucleotide in accordance with the invention comprises at least one MOE nucleoside, typically and preferably, at least 2, 3, 4, 5, 6, 7, 8, 9, 10, 11, 12, 20, 30, 40, 50 or even more MOE nucleosides. In a further preferred embodiment, said MOE oligonucleotide comprises at least two adjacent MOE nucleosides, wherein said phosphorothioate internucleoside linkage between said at least two adjacent MOE nucleosides is stereospecific Sp or Rp. In a further preferred embodiment, said MOE oligonucleotide comprises at least 3, 4, 5, 6, 7, 8, 9, 10, 11, 12, 15, 20, 25, 30 or even more consecutive MOE nucleosides, wherein said phosphorothioate internucleoside linkage between said at least 3, 4, 5, 6, 7, 8, 9, 10, 11, 12 15, 20, 25, 30 or even more consecutive MOE nucleosides is stereospecific Sp or Rp.

Thus, the inventive method provides for a stereodefined phosphorothioate MOE oligonucleotide comprising at least one stereospecific phosphorothioate nucleotide pair wherein the phosphorothioate internucleoside linkage between the nucleotides pair is either in the Rp configuration or in the Sp configuration, and wherein at least one of the nucleosides of the nucleotide pair is a MOE nucleotide. The MOE oligonucleotide is at least 3 nucleotides in length, and may for example have a length of 7-100, preferably 7-70, further preferably 7-30 nucleotides.

DETAILED DESCRIPTION OF THE INVENTION

Unless defined otherwise, all technical and scientific terms used herein have the same meanings as commonly understood by one of ordinary skill in the art to which this invention belongs.

Each "alkyl" moiety either alone or as part of a larger group such as alkoxy or alkylene is a straight or branched carbon chain and is preferably $C_1$-$C_{10}$alkyl, more preferably $C_1$-$C_6$alkyl, and again more preferably more preferably $C_1$-$C_4$alkyl. Examples include methyl, ethyl, n-propyl, prop-2-yl (iso-propyl), n-butyl, tert-butyl, but-2-yl, 2-methyl-prop-1-yl or 2-methyl-prop-2-yl. Examples of an alkoxy include methoxy, ethoxy, propoxy, iso-propoxy, n-butoxy, sec-butoxy, tert-butoxy, n-pentoxy, neo-pentoxy, n-hexoxy. As described herein, alkoxy may include further substituents such as halogen atoms leading to haloalkoxy moieties.

Halogen is fluorine, chlorine, bromine or iodine.

Each haloalkyl moiety either alone or as part of a larger group such as haloalkoxy is an alkyl group substituted by one or more of the same or different halogen atoms. Examples include difluoromethyl, trifluoromethyl, chlorodifluoromethyl and 2,2,2-trifluoro-ethyl. Haloalkyl moieties include for example 1 to 5 halo substituents, or 1 to 3 halo substituents.

Each "alkylene" moiety is a straight or branched carbon chain and is, for example, —$CH_2$—, —$CH_2$—$CH_2$—, —$CH(CH_3)$—, —$CH_2$—$CH_2$—$CH_2$—, —$CH(CH_3)$—$CH_2$— or —$CH(CH_2CH_3)$—.

Each "cycloalkyl" moiety can be in mono- or bi-cyclic form, typically and preferably in mono-cyclic form, and preferably contains 3 to 8 carbon atoms, more preferably 3 to 7 carbon atoms. Examples of monocyclic cycloalkyl groups include cyclopropyl, cyclobutyl and cyclohexyl.

The term "aryl" (abbreviated as "Ar"), as used herein, refers to an aromatic ring wherein each of the atoms forming the ring is a carbon atom. Aryl rings are formed by five, six, seven, eight, nine, or more than nine carbon atoms. Aryl groups are unsubstituted or substituted. Preferably, the term "aryl", as used herein, refers to a $C_6$-$C_{10}$aryl optionally substituted with halogen, $C_1$-$C_6$alkyl, $C_3$-$C_6$cycloalkyl, $C_1$-$C_4$alkoxy. Examples of a $C_6$-$C_{10}$aryl are phenyl, biphenyl, naphthyl, anthracyl, indanyl, phthalimidyl, naphthimidyl, phenanthridinyl, and tetrahydronaphthyl. In a further preferred embodiment, the term "aryl", as used herein, refers to phenyl optionally substituted with halogen, $C_1$-$C_6$alkyl, $C_3$-$C_6$cycloalkyl, $C_1$-$C_4$alkoxy.

The term "aralkyl", as used herein, refers to an alkyl group substituted with an aryl group. Suitable aralkyl groups include benzyl, picolyl, and the like, all of which may be optionally substituted.

An "aryloxy" group, as used herein, refers to an aryl group linked to oxygen i.e. (aryl)-O-group, where the aryl is as defined herein. An example includes phenoxy (—$OC_6H_5$) group optionally substituted with halogen, $C_1$-$C_6$alkyl, $C_1$-$C_4$alkoxy.

An "aryloxyalkyl" group as used herein, refers to an aryl group linked to oxygen, i.e. (aryl)-O— group, which is further linked to an alkyl, i.e. (aryl)-O-(alkyl) group, where the alkyl and aryl are as defined herein. An example includes the ($CH_2$—$OC_6H_5$) group optionally substituted preferably with halogen, $C_1$-$C_6$alkyl, $C_1$-$C_4$alkoxy.

An "acyl group", as used herein, refers to an alkyl(C=O), aryl(C=O), aralkyl(C=O) or aryloxyalkyl(C=O) group, all of which independently of each other optionally substituted preferably with halogen, $C_1$-$C_6$alkyl, $C_1$-$C_4$alkoxy. An acyl moiety can have an intervening moiety (Y) that is oxy, amino, thio, or seleno between the carbonyl and the hydrocarbon group. For example, an acyl group can be alkyl-Y—(C=O), aryl-Y—(C=O), aralkyl-Y—(C=O) or aryloxyalkyl-Y—(C=O).

Where a group is said to be optionally substituted, preferably there are optionally 1-3 substituents, more preferably optionally 1-2 substituents, very preferably optionally one substituent. Where a group is said to be optionally substituted, and where there are more than one substituents for said optional substitution of said group, said more than one substituents can either be the same or different.

The term "protecting group," as used herein, is well known in the art and includes those described in detail in *Protecting Groups in Organic Synthesis*, T. W. Greene and P. G. M. Wuts, 3rd edition, John Wiley & Sons, 1999, and in *Current Protocols in Nucleic Acid Chemistry*, edited by S. L. Beaucage et al. Jun. 2012, and hereby in particular in Chapter 2.

Suitable amino-protecting groups include carbamates such as methyl carbamate, ethyl carbamate, 9-fluorenylmethyl carbamate (Fmoc), 9-(2-sulfo)fluorenylmethyl carbamate, 2,7-di-t-butyl-[9-(10,10-dioxo-10,10,10,10-tetrahydrothioxanthyl]methylcarbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1,1-dimethyl-2,2-dibromoethyl carbamate (DB-t-BOC), 1,1-dimethyl-2,2,2-trichloroethyl carbamate (TCBOC), benzyl carbamate (Cbz), p-methoxybenzyl carbamate (Moz) and 2,4,6-trimethylbenzyl carbamate; as well as formamide, acetamide, benzamide.

Suitable hydroxyl protecting groups R include acetyl, t-butyl, t-butoxymethyl, methoxymethyl, tetrahydropyranyl, 1-ethoxy ethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, 4-monomethoxytrityl (MMTr), 4,4'dimethoxytrityl, (DMTr) and 4,4',4"-trimethoxytrityl (TMTr), 2-cyanoethyl (CE or Cne), 2-(trimethylsilyl)ethyl (TSE), 2-(2-nitrophenyl)ethyl, 2-(4-cyanophenyl)ethyl 2-(4-nitrophenyl)ethyl (NPE), 2-(4-nitrophenylsulfonyl)ethyl, 3,5-dichlorophenyl, 2,4-dimethylphenyl, 2-nitrophenyl, 4-nitrophenyl, 2,4,6-trimethylphenyl, 2-(2-nitrophenyl)ethyl, butylthiocarbonyl, 4,4',4"-tris (benzoyloxy)trityl, diphenylcarbamoyl, levulinyl, 2-(dibromomethyl)benzoyl (Dbmb), 2-(isopropylthiomethoxymethyl)benzoyl (Ptmt), 9-phenylxanthen-9-yl (pixyl) or 9-(p-methoxyphenyl)xanthine-9-y 1 (MOX). In some embodiments, each of the hydroxyl protecting groups R is independently selected from acetyl, benzyl, t-butyldimethylsilyl, t-butyldiphenylsilyl, trityl, 4-monomethoxytrityl, 4,4'-dimethoxytrityl, 4,4',4"-trimethoxytrityl, 9-phenylxanthin-9-yl (Pixyl) and 9-(p-methoxyphenyl)xanthin-9-yl (MOX). In preferred embodiments, each of the hydroxyl protecting groups R is independently selected from triphenylmethyl (trityl), 4-monomethoxytrityl, 4,4'-dimethoxytrityl, 4,4',4"-trimethoxytrityl, 9-phenylxanthin-9-yl (Pixyl) and 9-(p-methoxyphenyl)xanthin-9-yl (MOX). In further preferred embodiments, each of the hydroxyl protecting groups R is independently selected from trityl, 4-monomethoxytrityl and 4,4'-dimethoxytrityl group. In a very preferred embodiment, said hydroxyl protecting group R is selected from triphenylmethyl (trityl), 4-monomethoxytrityl, 4,4'-dimethoxytrityl, 4,4',4"-trimethoxytrityl, 9-phenylxanthin-9-yl (Pixyl) and 9-(p-methoxyphenyl)xanthin-9-yl (MOX). In a gain a very preferred embodiment, hydroxyl protecting group R is 4,4'-dimethoxytrityl or 4-monomethoxytrityl.

The term "nucleobase" (abbreviated as "Bn"), as used herein, refers to (i) adenine (A), (ii) cytosine (C), (iii) 5-methylcytosine (MeC), (iv) guanine (G), (v) uracil (U), or (vi) 5-methyluracil (MeU), or to a derivative of (i), (ii), (iii), (iv), (v) or (vi). The terms "derivative" of (i), (ii), (iii), (iv), (v) or (vi), and "nucleobase derivative" are used herein interchangeably.

Derivatives of (i), (ii), (iii), (iv), (v) or (vi), and nucleobase derivatives, respectively, are known to the skilled person in the art and are described, for example, in Sharma V. K. et al., Med. Chem. Commun., 2014, 5, 1454-1471. Preferred nucleobase derivatives include methylated adenine, guanine, uracil and cytosine and nucleobase derivatives, preferably of (i), (ii), (iii) or (iv), wherein the respective amino groups, preferably the exocyclic amino groups, are protected by acyl protecting groups or dialkylformamidino, preferably dimethylformamidino (DMF), and further include nucleobase derivatives such as 2-fluorouracil, 2-fluorocytosine, 5-bromouracil, 5-iodouracil, 2,6-diaminopurine, azacytosine and pyrimidine analogs such as pseudoisocytosine and pseudouracil.

In a further preferred embodiment, said nucleobase derivative is selected from methylated adenine, methylated guanine, methylated uracil and methylated cytosine, and from a nucleobase derivative of (i), (ii), (iii) or (iv), wherein the respective amino groups, preferably the exocyclic amino groups, are protected by a protecting group.

In a further preferred embodiment, said nucleobase derivative is selected from methylated adenine, methylated guanine, methylated uracil and methylated cytosine, and from a nucleobase derivative of (i), (ii), (iii) or (iv), wherein the respective amino groups, preferably the exocyclic amino groups, are protected by acyl protecting groups or dialkylformamidino, preferably dimethylformamidino (DMF).

In a further preferred embodiment, said nucleobase derivative is selected from a nucleobase derivative of (i), (ii), (iii) or (iv), wherein the respective amino groups, preferably the exocyclic amino groups, are protected by a protecting group.

In a further preferred embodiment, said nucleobase derivative is a nucleobase derivative of (i), (ii), (iii) or (iv), wherein the exocyclic amino groups, are protected by acyl protecting groups or dialkylformamidino, preferably dimethylformamidino (DMF).

In a further very preferred embodiment, said acyl protecting group of said exocyclic amino group of said nucleobase derivative of (i), (ii), (iii) or (iv) is —C(O)—$R^1$, wherein independently of each other $R^1$ is selected from $C_1$-$C_{10}$alkyl, $C_6$-$C_{10}$aryl, $C_6$-$C_{10}$aryl$C_1$-$C_{10}$alkylene, or $C_6$-$C_{10}$aryloxy$C_1$-$C_{10}$alkylene and wherein said dialkylformamidino protecting group is =C(H)—$NR^2R^3$, wherein $R^2$ and $R^3$ are independently of each other selected from $C_1$-$C_4$alkyl.

In a further very preferred embodiment, said acyl protecting group of said exocyclic amino group of said nucleobase derivative of (i), (ii), (iii) or (iv) is —C(O)—$R^1$, wherein independently of each other $R^1$ is selected from $C_1$-$C_4$alkyl; phenyl; phenyl substituted with halogen, $C_1$-$C_6$alkyl, $C_3$-$C_6$cycloalkyl, $C_1$-$C_4$alkoxy; benzyl; benzyl substituted with halogen, $C_1$-$C_6$alkyl, $C_3$-$C_6$cycloalkyl, $C_1$-$C_4$alkoxy; or phenyloxy$C_1$-$C_2$alkylene optionally substituted with halogen, $C_1$-$C_6$alkyl, $C_1$-$C_4$alkoxy; and wherein said dialkylformamidino protecting group is =C(H)—$NR^2R^3$, wherein $R^2$ and $R^3$ are independently of each other selected from $C_1$-$C_4$alkyl.

In a further very preferred embodiment, said acyl protecting group of said exocyclic amino group of said nucleobase derivative of (i), (ii), (iii) or (iv) is —C(O)—$R^1$, wherein independently of each other $R^1$ is selected from $C_1$-$C_4$alkyl; phenyl; phenyl substituted with halogen, $C_1$-$C_4$alkyl, $C_5$-$C_6$cycloalkyl, $C_1$-$C_4$alkoxy; benzyl; benzyl substituted with halogen, $C_1$-$C_4$alkyl, $C_1$-$C_4$alkoxy; or phenyloxymethylene ($CH_2$—$OC_6H_5$) wherein the phenyl is optionally substituted with halogen, $C_1$-$C_4$alkyl, $C_5$-$C_6$cycloalkyl, $C_1$-$C_4$alkoxy; and wherein said dialkylformamidino protecting group is =C(H)—$NR^2R^3$, wherein $R^2$ and $R^3$ are independently of each other selected from $C_1$-$C_4$alkyl.

In a further very preferred embodiment, said acyl protecting group of said exocyclic amino group of said nucleobase derivative of (i), (ii), (iii) or (iv) is —C(O)—$R^1$, wherein independently of each other $R^1$ is selected from $C_1$-$C_3$alkyl; phenyl; phenyl substituted with $C_1$-$C_3$alkyl, methoxy; benzyl; benzyl substituted with $C_1$-$C_3$alkyl, methoxy; or phenyloxymethylene ($CH_2$—$OC_6H_5$) wherein the $C_6H_5$ is optionally substituted with $C_1$-$C_3$alkyl, methoxy; and wherein said dialkylformamidino protecting group is =C(H)—$NR^2R^3$, wherein $R^2$ and $R^3$ are independently of each other selected from $C_1$-$C_4$alkyl.

In a further very preferred embodiment, said acyl protecting group of said exocyclic amino group of said nucleobase derivative of (i), (ii), (iii) or (iv) is —C(O)—$R^1$, wherein independently of each other $R^1$ is selected from $C_1$-$C_3$alkyl; phenyl; phenyl substituted with $C_1$-$C_3$alkyl, methoxy; benzyl; benzyl substituted with $C_1$-$C_3$alkyl, methoxy; or phenyloxymethylene ($CH_2$—$OC_6H_5$) wherein the $C_6H_5$ is optionally substituted with $C_1$-$C_3$alkyl, methoxy; and wherein said dialkylformamidino protecting group is dimethylformamidino (DMF).

In a further very preferred embodiment, said acyl protecting group of said exocyclic amino group of said nucleobase derivative of (i), (ii), (iii) or (iv) is —C(O)—$R^1$, wherein independently of each other $R^1$ is selected from methyl, iso-propyl, phenyl, benzyl, or phenyloxymethylene ($CH_2$—$OC_6H_5$) wherein the $C_6H_5$ is optionally substituted with $C_1$-$C_3$alkyl, methoxy; and wherein said dialkylformamidino protecting group is dimethylformamidino (DMF).

In a further very preferred embodiment, said acyl protecting group of said exocyclic amino group of said nucleobase derivative of (i), (ii), (iii) or (iv) is —C(O)—$R^1$, wherein independently of each other $R^1$ is selected from methyl, iso-propyl, phenyl, benzyl, or phenyloxymethylene ($CH_2$—$OC_6H_5$) wherein the $C_6H_5$ is optionally substituted with methyl, iso-propyl; and wherein said dialkylformamidino protecting group is dimethylformamidino (DMF).

The term "dialkylformamidino", as used herein refers to =C(H)—$NR^2R^3$, wherein $R^2$ and $R^3$ are independently of each other selected from $C_1$-$C_4$alkyl. In preferred embodiments, said dialkylformamidino is a protecting group of said exocyclic amino group of said nucleobase derivative of (i), (ii), (iii) or (iv). The resulting compounds may be of either the (E)- or (Z)-configuration and both forms, and mixtures thereof in any ratio, should be included within the scope of the present invention. In a preferred embodiment the inventive compounds comprise the dialkylformamidino, preferably dimethylformamidino (DMF), in the (Z) configuration.

The terms "stereodefined", "stereocontrolled", "stereoselective" and "stereospecific" are used interchangeably herein and refer to a stereodefined internucleoside linkage between the nucleosides of the at least one stereospecific phosphorothioate nucleotide pair of the phosphorothioate MOE oligonucleotide of the present invention, wherein said internucleoside linkage between said nucleosides is either in the Sp configuration or in the Rp configuration.

Such stereodefined phosphorothioate MOE oligonucleotide is typically and preferably achieved by the use of the inventive compound of formula (Ia) or (Ib) in the course of the coupling step leading to said stereodefined internucleoside linkage on the 3' side of the newly incorporated nucleoside (or 5' of the grown oligonucleotide chain). It is recognized, however, that an inventive stereocontrolled MOE oligonucleotide may comprises small amount of the alternative stereoisomer at any one position, wherein typically and preferably said small amount of the alternative stereoisomer is less than 5%, preferably less than 4%, further preferably less than 3%, and again further preferably less than 2%.

The term "oligonucleotide", as used herein, refers to a nucleic acid sequence comprising 2 or more nucleotides, for example up to hundred or more, preferably at least 2 nucleotides to 100 nucleotides. Oligonucleotides are polyribonucleotides or polydeoxyribonucleotides or mixtures thereof and are preferably selected from unmodified RNA, unmodified DNA, modified RNA or modified DNA. The modification may comprise the backbone and/or the nucleotide analogues as further described herein. Oligonucleotides are preferably selected from single-stranded DNA, double-stranded DNA, single-stranded RNA or double-stranded DNA, further preferably from single-stranded. The term "modified oligonucleotide", such as modified RNA or modified DNA, as used herein, refers to an oligonucleotide as defined above and having at least one modified internucleoside linkage and/or at least one sugar modification and/or at least one base modification compared to a naturally occurring ribonucleotide- or deoxyribonucleotide-based oligonucleotide. A "modified internucleoside linkage" indicates the presence of a modified version of the phosphodiester which does not occur naturally in RNA and DNA. Examples of internucleoside linkage modifications, which are known to the skilled person in the art and which are compatible with the present invention, are and include in particular, phosphoramidate, phosphorodiamidate, phosphorothioate, phosphorodithioate, H-phosphonate, methyl phosphonate and methyl phosphonothioate. A "sugar modification" indicates the presence of a modified version of the ribosyl moiety as naturally occurring in RNA and DNA (i.e. the furanosyl moiety), such as bicyclic sugars, tetrahydropyrans, morpholinos, 2'-modified sugars, 3'-modified sugars, 4'-modified sugars, 5'-modified sugars, and 4'-substituted sugars. Examples of suitable sugar modifications are known to the skilled person in the art and include, but are not limited to, 2'-O-modified RNA nucleotide residues, such as 2'-O-alkyl or 2'-O-(substituted)alkyl e.g. 2'-O-methyl, 2'-O-(2-cyanoethyl), 2'-O-(2-methoxy)ethyl (2'-MOE), 2'-O-(2-thiomethyl)ethyl; 2'-O-(haloalkoxy)methyl e.g. 2'-O-(2-chloroethoxy)methyl (MCEM), 2'-O-(2,2-dichloroethoxy)methyl (DCEM); 2'-O-alkoxycarbonyl e.g. 2'-O-[2-(methoxycarbonyl)ethyl] (MOCE), 2'-O-[2-(N-methylcarbamoyl)ethyl] (MCE), 2'-O-[2-(N,N-dimethylcarbamoyl)ethyl] (DMCE), in particular a 2'-O-methyl modification or a 2'-O-(2-methoxy)ethyl (2'-MOE). Another important modification includes "bridged" or "bicylic" nucleic acid (BNA) modified sugar moieties, such as found in e.g. locked nucleic acid (LNA), xy/o-LNA, α-L-LNA, β-D-LNA, cEt (2'-O,4'-C constrained ethyl) LNA, cMOEt (2'-O,4'-C constrained methoxyethyl) LNA, ethylene-bridged nucleic acid (ENA), hexitol nucleic acid (HNA), fluorinated HNA (F-HNA), pyranosyl-RNA (p-RNA), 3'-deoxypyranosyl-DNA (p-DNA); or other modified sugar moieties, such as morpholino (PMO), cationic morpholino (PMOPlus) or PMO-X, all known to the skilled person in the art. The term "base modification", as used herein refers to the modification of a naturally occurring base in RNA and/or DNA (i.e. pyrimidine or purine base). A base modification is known to the skilled person in the art and includes, but is not limited to, a modified version of the natural purine and pyrimidine bases (e.g. adenine, uracil, guanine, cytosine, and thymine), such as hypoxanthine, pseudouracil, pseudothymine, 2-thiopyrimidine (e.g. 2-thiouracil, 2-thiothymine), 2,6-diaminopurine, 5-substituted pyrimidine (e.g. 5-halouracil, 5-methyluracil, 5-methylcytosine) 7-deazaguanine, 7-deazaadenine, 7-aza-2,6-diaminopurine, 8-aza-7-deazaguanine, 8-aza-7-deazaadenine, or 8-aza-7-deaza-2,6-diaminopurine. It is also encompassed by the invention that said oligonucleotide comprises more than one, the same or different, internucleoside linkage modification, sugar modification and/or base modification. Thus, oligonucleotides, as referred to in this invention can consist of any combinations of the nucleotides and their modifications described above and can have either a few, e.g. up to 20, or many, e.g. 20 to several hundred or more, nucleotides incorporated in their chain. Preferably, oligonucleotides of the present invention comprise at least 2 nucleotides to 300 nucleotides or their modifications described above.

The term "gapmer", as used herein, refers to an oligonucleotide strand characterized in that at least one internucleotidic phosphorus linkage of the oligonucleotide strand is a phosphate diester linkage, for example such as those found in naturally occurring DNA or RNA. Typically and preferably, more than one internucleotidic phosphorus linkage of the oligonucleotide strand is a phosphate diester linkage such as those found in naturally occurring DNA or RNA. Further typically and preferably, The term "gapmer", as used herein, refers to an oligonucleotide comprising a central block of deoxynucleotide monomers, typically and preferably sufficiently long to induce RNase H cleavage, said central block is flanked by blocks of MOE nucleotides of the invention, and preferably by blocks of inventive MOE oligonucleotides.

Thus, in a first aspect, the present invention provides for a compound of formula (Ia) or formula (Ib),

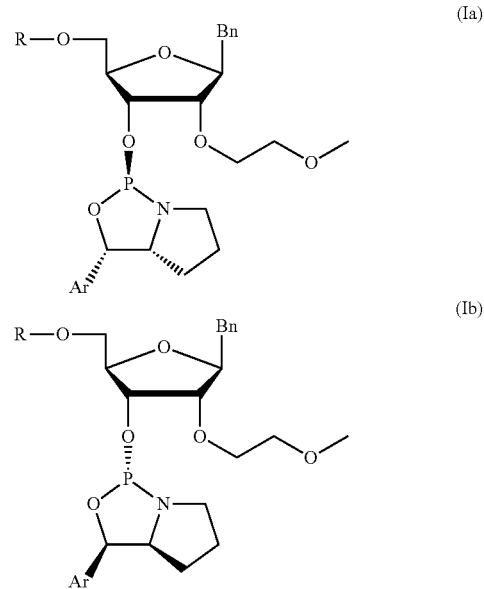

wherein Ar is phenyl (Ph, $C_6H_5$) optionally substituted with halogen, $C_1$-$C_6$alkyl, $C_3$-$C_6$cycloalkyl, $C_1$-$C_4$alkoxy; and R is a protective group of a hydroxyl group; and Bn is selected from (i) adenine, (ii) cytosine, (iii) 5-methylcytosine, (iv) guanine, (v) uracil, (vi) 5-methyluracil, or (vii) a derivative of (i), (ii), (iii), (iv), (v) or (vi).

In a preferred embodiment, said Ar is phenyl optionally substituted with halogen, $C_1$-$C_6$alkyl, $C_3$-$C_6$cycloalkyl, $C_1$-$C_4$alkoxy.

In a very preferred embodiment, Ar is phenyl. Thus, in such a very preferred embodiment, said compound of formula (Ia) is a compound of formula (IIa) and said compound of formula (Ib) is a compound of formula (IIb)

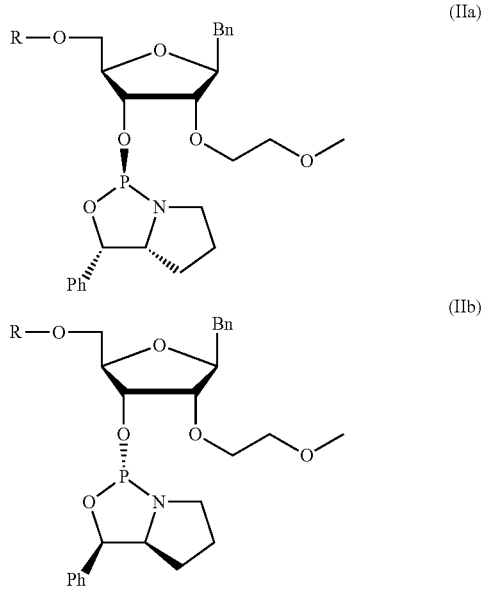

wherein R and Bn are defined as described above and herein.

In a further very preferred embodiment, said R is selected from triphenylmethyl (trityl), 4-monomethoxytrityl (MMTr), 4,4'-dimethoxytrityl (DMTr), 4,4',4''-trimethoxytrityl, 9-phenylxanthin-9-yl (Pixyl) and 9-(p-methoxyphenyl)xanthin-9-yl (MOX), and wherein preferably said R is 4,4'-dimethoxytrityl (DMTr) or 4-monomethoxytrityl (MMTr). Thus, in a further very preferred embodiment, said Ar is phenyl and said R is 4,4'-dimethoxytrityl (DMTr) or 4-monomethoxytrityl (MMTr).

In a further very preferred embodiment, said derivative is derived from said adenine, cytosine, 5-methylcytosine or said guanine, wherein the exocyclic amino group of said adenine, cytosine, 5-methylcytosine or said guanine is protected by a protecting group, wherein preferably said is an acyl protecting group or dialkylformamidino, preferably dimethylformamidino (DMF).

In a further very preferred embodiment, said protecting group is independently of each other selected from —C(O)—$R^1$, wherein independently of each other $R^1$ is selected from $C_1$-$C_{10}$alkyl, $C_6$-$C_{10}$aryl, $C_6$-$C_{10}$aryl$C_1$-$C_{10}$alkylene, or $C_6$-$C_{10}$aryloxy$C_1$-$C_{10}$alkylene and wherein said dialkylformamidino protecting group is =C(H)—$NR^2R^3$, wherein $R^2$ and $R^3$ are independently of each other selected from $C_1$-$C_4$alkyl.

In a further very preferred embodiment, said protecting group is independently of each other selected from —C(O)—$R^1$, wherein independently of each other $R^1$ is selected from $C_1$-$C_3$alkyl; phenyl; phenyl substituted with $C_1$-$C_3$alkyl, methoxy; benzyl; benzyl substituted with $C_1$-$C_3$alkyl, methoxy; or phenyloxymethylene ($CH_2$—$OC_6H_5$) wherein the $C_6H_5$ is optionally substituted with $C_1$-$C_3$alkyl, methoxy; and wherein said dialkylformamidino protecting group is dimethylformamidino (DMF).

In a further very preferred embodiment, said protecting group is independently of each other selected from —C(O)—$R^1$, wherein independently of each other $R^1$ is selected from methyl, iso-propyl, phenyl, $CH_2$—$OC_6H_5$ wherein the $C_6H_5$ is optionally substituted with iso-propyl; and wherein said dialkylformamidino protecting group is dimethylformamidino (DMF).

Thus, in a very preferred embodiment, said derivative is derived from said adenine, cytosine, 5-methylcytosine or said guanine, wherein the exocyclic amino group of said adenine, cytosine, 5-methylcytosine or said guanine is protected by a protecting group, which is independently of each other selected from —C(O)—$R^1$, wherein independently of each other $R^1$ is selected from methyl, iso-propyl, phenyl, $CH_2$—$OC_6H_5$ wherein the $C_6H_5$ is optionally substituted with iso-propyl; and wherein said dialkylformamidino protecting group is dimethylformamidino (DMF), and thus comprise the formulas depicted below (iso-butyryl, phenoxy acetyl, 4-isopropylphenoxyacetyl, DMF).

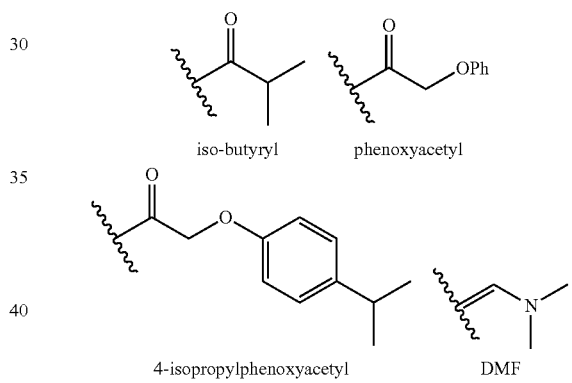

Thus, in a further very preferred embodiment, said Bn represents adenine or a derivative of adenine, wherein said derivative of adenine is derived from said adenine, wherein the exocyclic amino group of said adenine is protected by a protecting group, and wherein said protecting group is selected from (i) —C(O)—Ph or (ii) from the formulas depicted below (iso-butyryl, phenoxy acetyl).

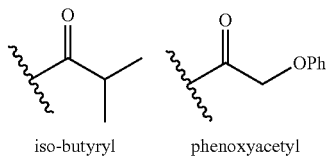

In a further very preferred embodiment, said Bn represents cytosine or 5-methylcytosine, or a derivative thereof, wherein said derivative is derived from said cytosine or 5-methylcytosine, wherein the exocyclic amino group of said cytosine, or 5-methylcytosine is protected by a protecting group, and wherein said protecting group is selected from —C(O)—Ph or —C(O)—$CH_3$.

In a further very preferred embodiment, said Bn represents cytosine or a derivative thereof, wherein said derivative is derived from said cytosine, wherein the exocyclic amino group of said cytosine is protected by a protecting group, and wherein said protecting group is selected from —C(O)—Ph or —C(O)—CH$_3$.

In a further very preferred embodiment, said Bn represents guanine or a derivative of guanine, wherein said derivative of guanine is derived from said guanine, wherein the exocyclic amino group of said guanine is protected by a protecting group, and wherein said protecting group is selected from the formulas depicted below (iso-butyryl, 4-isopropylphenoxy acetyl, DMF).

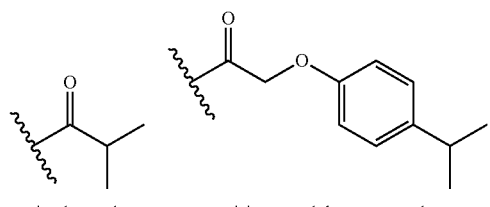

iso-butyryl     4-isopropylphenoxyacetyl

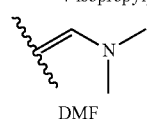

DMF

In a further very preferred embodiment, said the compound is represented by formula Sp-6a, Sp-6b, Sp-6c, Sp-6d, Sp-6e, Sp-6f, Rp-6a, Rp-6b, Rp-6c, Rp-6d, Rp-6e, or Rp-6f.

Sp-6a

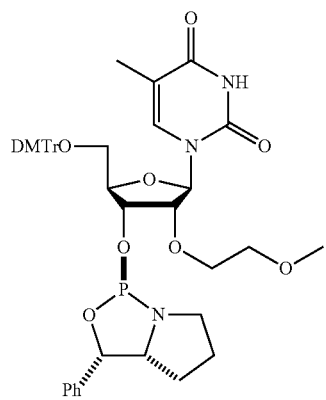

Sp-6b

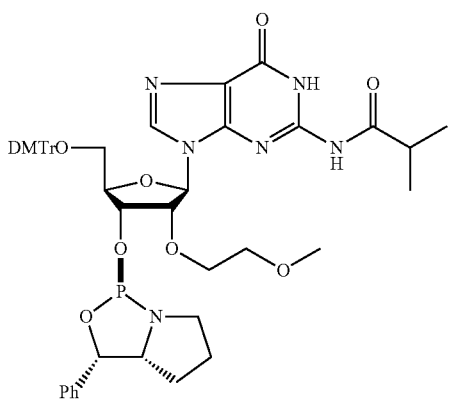

Sp-6c

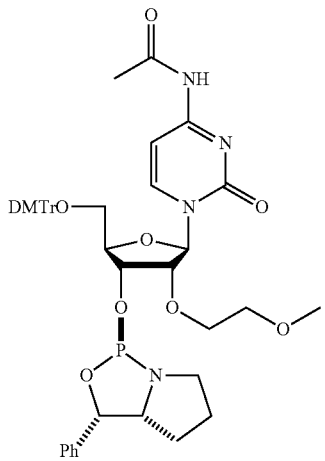

Sp-6d

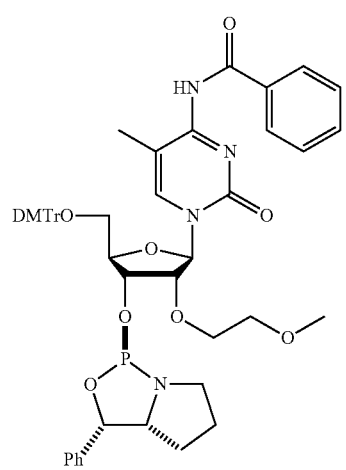

Sp-6e

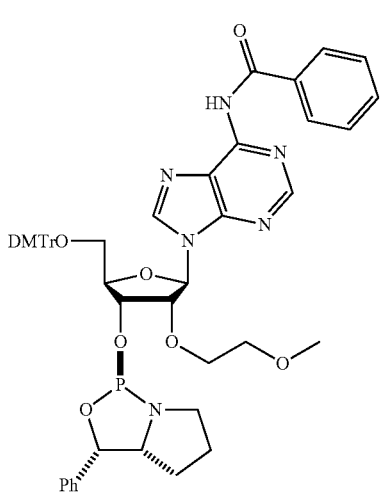

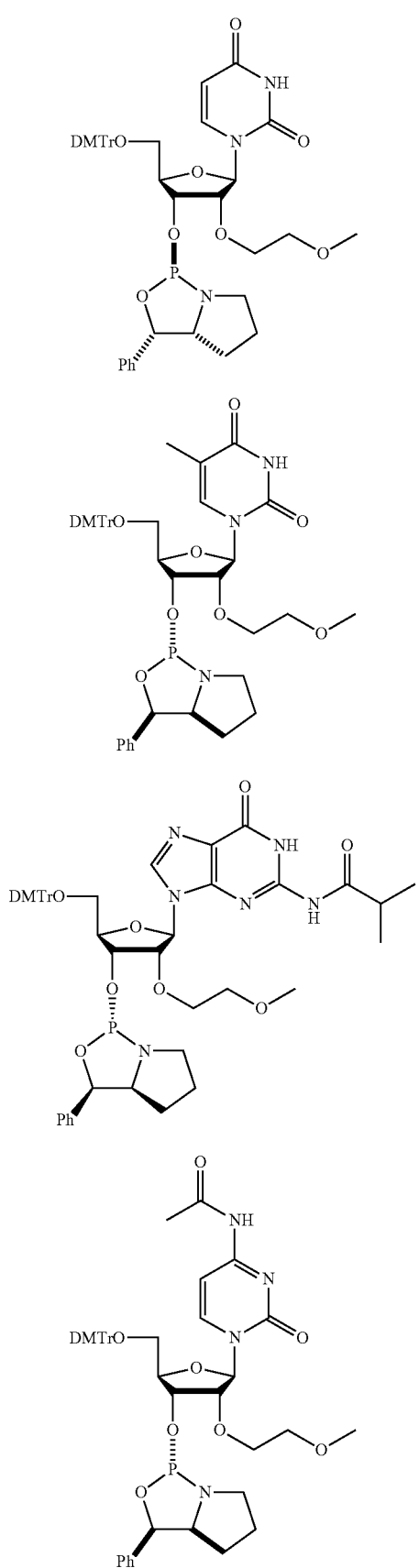

Sp-6f

Rp-6a

Rp-6b

Rp-6c

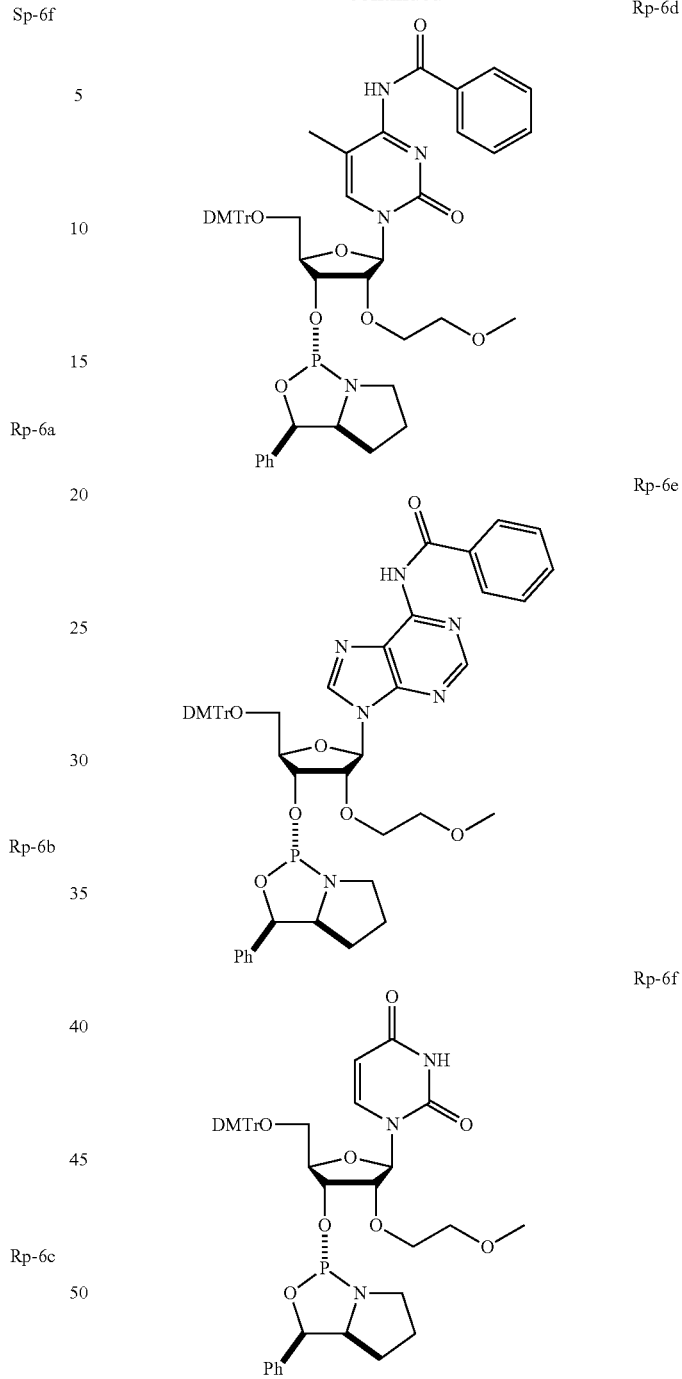

Rp-6d

Rp-6e

Rp-6f

Moreover, in a further aspect, the present invention provides for a method for synthesizing a stereodefined phosphorothioate MOE oligonucleotide comprising the step of coupling an inventive compound of formula (Ia) or formula (Ib) to either an oligonucleotide synthesis support or a preceding nucleotide, wherein said stereodefined phosphorothioate MOE oligonucleotide comprises at least one stereospecific phosphorothioate nucleotide pair wherein the internucleoside linkage between the nucleosides of the at least one stereospecific phosphorothioate nucleotide pair is either in the Sp configuration or in the Rp configuration, and wherein at least one of the nucleosides of the at least one stereospecific phosphorothioate nucleotide pair is a MOE nucleoside. A MOE nucleoside comprises a 2'-O-(2-methoxy)ethyl (MOE) ribose sugar modification. Thus, a MOE oligonucleotide in accordance with the invention comprises at least one MOE nucleoside, typically and preferably, at least 2, 3, 4, 5, 6, 7, 8, 9, 10, 11 or 12 MOE nucleosides. In a further preferred embodiment, said MOE oligonucleotide comprises at least two adjacent MOE nucleosides, wherein said phosphorothioate internucleoside linkage between said at least two adjacent MOE nucleosides is stereospecific Sp or Rp. In a further preferred embodiment, said MOE oligonucleotide comprises at least 3, 4, 5, 6, 7, 8, 9, 10, 11 or 12 consecutive MOE nucleosides, wherein typically and preferably said phosphorothioate internucleoside linkage between said at least 3, 4, 5, 6, 7, 8, 9, 10, 11 or 12 consecutive MOE nucleosides is stereospecific Sp or Rp.

Thus, the inventive method provides for a stereodefined phosphorothioate MOE oligonucleotide comprising at least one stereospecific phosphorothioate nucleotide pair wherein the phosphorothioate internucleoside linkage between the nucleotides pair is either in the Rp configuration or in the Sp configuration, and wherein at least one of the nucleosides of the nucleotide pair is a MOE nucleotide. The MOE oligonucleotide is at least 3 nucleotides in length, and may for example have a length of 7-100, preferably 7-70, further preferably 7-30 nucleotides.

Thus, the invention provides for a method of synthesizing a MOE oligonucleotide said method comprising the steps of coupling the compound of formula (Ia) or (Ib) of the invention to either an oligonucleotide synthesis support, or a preceding nucleotide. The method may use standard phosphoramidite synthesis protocols, although variations in said synthesis protocol such as extended coupling times or the like are within the scope of the present invention.

Standard phosphoramidite synthesis protocols are known to the skilled person in the art, and have been extensively described. As examples, it is referred to Wan et al, (Nucleic Acids Res. (2014) 42:13456-13468) and WO2014/010250 as well as to McBride et al. (Tetrahedron Lett., (1983) 24:245-248) and Beaucage et al. (Curr Protoc Nucleic Acid Chem (2000) 3.3.1-3.3.20) and U.S. Pat. No. 5,750,666; each of which is incorporated herein in its entirety.

A general description of a standard oligonucleotide synthesis protocol is as follows. Oligonucleotide synthesis typically begins with the 3'-most nucleotide and proceeds through a series of cycles composed of four steps that are repeated until the 5'-most nucleotide is attached. However, it is within the ordinary skill of the artisan to establish oligonucleotide synthesis in 5'-3' direction by choosing the first nucleoside and the nucleoside phosphoramidite in the appropriate conformation. The inventive methods are applicable in both directions of synthesis, wherein synthesis in 3'-5' direction is generally preferred.

The four steps are deprotection, coupling, capping and stabilization (generally oxidation or sulfurization). In one variation, during the deprotection step the trityl group attached to the 5'-carbon of the pentose sugar of the recipient nucleotide is removed by trichloroacetic acid (TCA) or dichloroacetic acid (DCA) in a suitable solvent such as dichloromethane or toluene, leaving a reactive hydroxyl group. The next phosphoramidite monomer is added in the coupling step. An activator such as tetrazole, a weak acid, is used to react with the coupling nucleoside phosphoramidite, forming a tetrazolyl phosphoramidite intermediate. This intermediate then reacts with the hydroxyl group of the recipient and the 5' to 3' linkage is formed. The tetrazole is reconstituted and the process continues. A coupling failure results in an oligonucleotide still having a reactive hydroxyl group on the 5'-end. To prevent these oligonucleotides from remaining reactive for the next cycle (which would produce an oligonucleotide with a missing nucleotide), they are removed from further synthesis by being irreversibly capped by an acetylating reagent such as a mixture of acetic anhydride and N-methylimidazole. This reagent reacts only with the free hydroxyl groups to cap the oligonucleotides.

In the oxidation or sulfurization step, the phosphite linkage between the growing oligonucleotide and the most recently added nucleotide is stabilized to generate either phosphotriester or phosphorothioate internucleoside linkages, wherein in standard phosphoramidite syntheses, phosphorothioate oligonucleotides are synthesized as a random mixture of Rp and Sp phosphorothioate linkages.

Thus, in a further preferred embodiment of the inventive method, said method comprises said coupling step, and further comprises the steps of capping, sulfurization and deprotecting, and repeating said steps until a desired length of said MOE oligonucleotide is achieved.

In a preferred embodiment, said method for synthesizing a stereodefined phosphorothioate MOE oligonucleotide comprising the step of coupling the inventive compound of formula (Ia) or formula (Ib) to either an oligonucleotide synthesis support or a preceding nucleotide, wherein said stereodefined phosphorothioate MOE oligonucleotide comprises at least one stereospecific phosphorothioate nucleotide pair wherein the internucleoside linkage between the nucleosides of the at least one stereospecific phosphorothioate nucleotide pair is either in the Sp configuration or in the Rp configuration, and wherein at least one of the nucleosides of the at least one stereospecific phosphorothioate nucleotide pair is a MOE nucleoside.

In a further preferred embodiment, said other nucleoside of the at least one stereospecific phosphorothioate nucleotide pair is a DNA or a modified DNA. In a further preferred embodiment, said other nucleoside of the at least one stereospecific phosphorothioate nucleotide pair is other than DNA, and wherein preferably aid other nucleoside of the at least one stereospecific phosphorothioate nucleotide pair is a 2' substituted nucleoside. In a further preferred embodiment, both nucleosides of the at least one stereospecific phosphorothioate nucleotide pair are a MOE nucleoside.

In a further preferred embodiment of the inventive method, said MOE oligonucleotide comprises at least two adjacent MOE nucleosides, and wherein said phosphorothioate internucleoside linkage between at least two adjacent MOE nucleosides is stereospecific Sp or Rp. In a further preferred embodiment of the inventive method, all the phosphorothioate internucleoside linkages between adjacent MOE nucleosides are stereospecific.

In a further preferred embodiment, said phosphorothioate MOE oligonucleotide is chirally pure. Chirally pure, as used herein, refers to the stereodefined phosphorothioate MOE oligonucleotide of the present invention, wherein all of said phosphorothioate internucleoside linkages between MOE nucleosides are stereospecific Sp or Rp. In a further preferred embodiment, said phosphorothioate MOE oligonucleotide is chirally uniform. Chirally uniform, as used herein, refers to the stereodefined phosphorothioate MOE oligonucleotide of the present invention, wherein all of said phosphorothioate internucleoside linkages between MOE nucleosides are stereospecific either all Sp or either all Rp.

In a further preferred embodiment, said MOE oligonucleotide is comprised by a gapmer oligonucleotide. In a further preferred embodiment, each wing of said gapmer comprises an inventive MOE oligonucleotide, and wherein each wing of said gapmer comprises one or more stereospecific phosphorothioate internucleoside linkage between at least two adjacent MOE nucleosides comprised by said MOE oligonucleotides. In a further preferred embodiment, said gapmer comprises in each wing an inventive MOE oligonucleotide, and wherein each of said inventive MOE oligonucleotide comprises at least two adjacent MOE nucleosides, and wherein said phosphorothioate internucleoside linkage between said at least two adjacent MOE nucleosides is stereospecific Sp or Rp. In a further preferred embodiment, In a further preferred embodiment, said gapmer comprises in each wing an inventive MOE oligonucleotide, and wherein each of said inventive MOE oligonucleotide comprises at least 3, 4, 5, 6, 7, 8, 9, 10, 11 or 12 consecutive MOE nucleosides, wherein typically and preferably said phosphorothioate internucleoside linkage between said at least 3, 4, 5, 6, 7, 8, 9, 10, 11 or 12 consecutive MOE nucleosides is stereospecific Sp or Rp. In a further preferred embodiment, said gapmer comprises in each wing an inventive MOE oligonucleotide, wherein each of said MOE oligonucleotide is chirally pure. In a further preferred embodiment, said gapmer comprises in each wing an inventive MOE oligonucleotide, wherein each of said MOE oligonucleotide is chirally uniform.

EXAMPLES

Example 1

Synthesis of Inventive Chiral Phosphoramidites

The syntheses of very preferred chiral phosphoramidites 6 of the invention is described in the following. In view of the general formula (I), these preferred chiral phosphoramidites 6 comprise the 4,4'-dimethoxytrityl group as protective group of the 5'-OH group and phenyl as the aryl substituent of the oxazaphospholidine moiety. Specific chiral phosphoramidites 6 with different nucleobases and nucleobase derivatives were prepared as described in the subsequent example. The corresponding nucleosides comprising said nucleobases and nucleobase derivatives, respectively, were synthesized according to published procedures (B. S. Ross, et al., *Nucleosides, Nucleotides, and Nucleic Acids* (2005) 24(5-7):815-818; S. Shabbir Ali et al., *Nucleosides, Nucleotides, and Nucleic Acids* (2008) 27:1024-1033). The assignment of the configurations were confirmed and based on the $^2J_{pc}$ values of the oxazaphospholidine ring.

The below reaction scheme illustrates the synthesis, by way of example, for the Sp-6 compounds. The corresponding Rp-6 were prepared in an analogously manner starting from L-Proline and compound 5L, respectively.

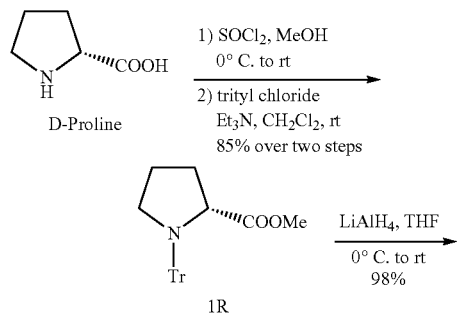

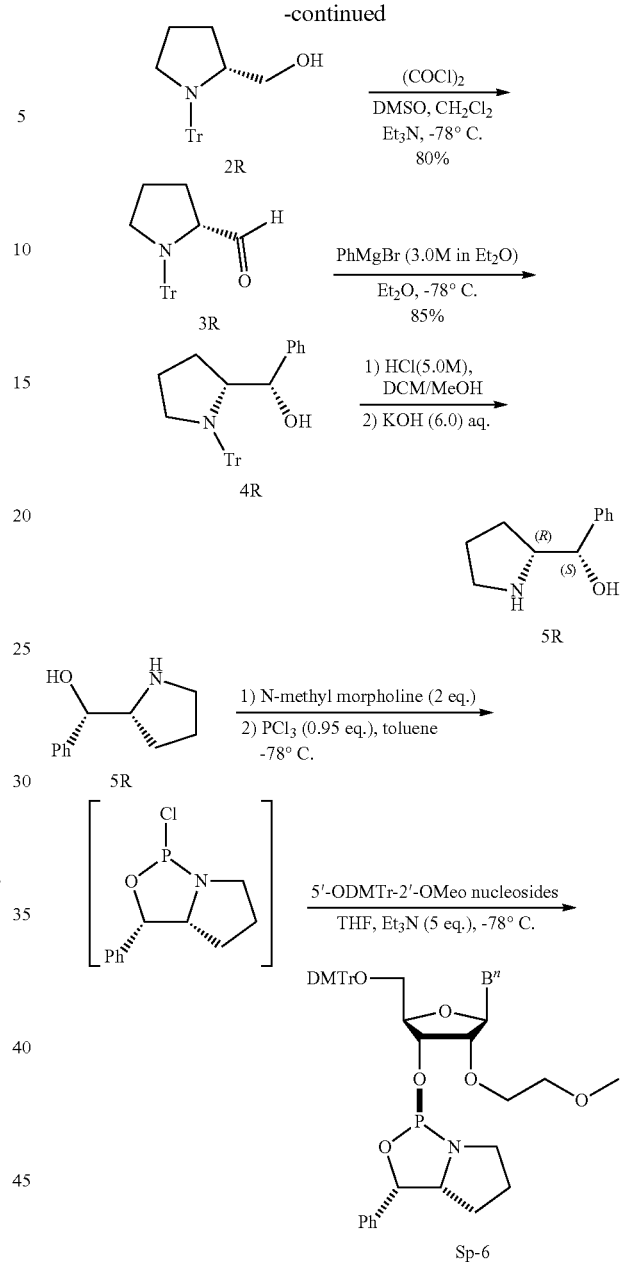

The trityl protected aldehyde 3R was prepared from enantiomerically-pure D-proline following a reported procedure (Journal of the American Chemical Society 2008, 130 (24), 7562).

Synthesis of Compound 4R

To a 500 ml round bottom flask was added compound 3R (14.5 g, 42.5 mmol) under Argon, followed by anhydrous diethyl ether (160 ml). The reaction was cooled down to −78° C. using dry ice/acetone, and phenyl magnesium bromide (3.0 M in diethyl ether, 28 ml, 85 mmol) was added dropwise. After the addition was complete, the reaction continued to stir under Argon for 6 hours at −78° C. The reaction was then quenched −78° C. by adding, dropwise, a 60 ml solution mixture (2/1) of saturated aqueous NH$_4$Cl and NH$_3$ (25% in water). The reaction was then allowed to warm to room temperature, and the two layers were separated. The aqueous layer was extracted twice with ethyl acetate, and the combined organic phases were dried over anhydrous Na$_2$SO$_4$, filtered and concentrated. The product was recrystallized in MeOH (30 ml). The solids were collected by filtration and dried under high vacuum to give 4R as a white solid (15.0 g, 85% yield).

Synthesis of Compound SR

To a 250 ml round bottom flask was placed compound 4R (15 g, 35.8 mmol) followed by 1:1 MeOH/DCM (20 ml) at room temperature. HCl (5.0 M aqueous solution, 30 ml) was added, and after 3 hours of vigorous stirring, the MeOH and DCM were evaporated, leaving the aqueous layer behind. The aqueous layer was extracted with 3×30 ml diethyl ether to remove the trityl byproduct. The aqueous phase was concentrated to dryness. The amino alcohol hydrochloride salt was recrystallized from 2-propanol (30 ml). The solid was suspended in DCM (60 ml) and was washed with 2 M KOH (60 ml). The aqueous layer was back extracted with DCM (3×60 ml). The organic layers were then dried over Na$_2$SO$_4$ and then evaporated under reduced pressure to afford compound 5R.

Compounds 4L and 5L were prepared in an identical procedure from L-proline.

Example 2

Synthesis of Preferred Specific Chiral Phosphoramidites

This example describes the syntheses of very preferred specific chiral phosphoramidites of the present invention.

Synthesis of Sp-6a (Sp-6-MeU)

All glassware were dried thoroughly prior to use. Triethylamine was distilled Et$_3$N was distilled from CaH$_2$, and stored over KOH pellets under Ar. N-methyl morpholine was distilled from BaO, and stored over KOH pellets under Ar.

Amino alcohol SR (533 mg, 3 mmol) was co-evaporated with anhydrous toluene three times and was dissolved in anhydrous toluene (3 mL) in a 25 ml round bottom flask with stirring under Argon. To this solution was added N-methyl morpholine (0.66 ml, 6 mmol). A second round bottom flask was charged with anhydrous toluene (5 ml) and phosphorus trichloride (0.25 ml, 2.85 mmol) at −70° C. with stirring under Argon. The amino alcohol solution was transferred to the solution of PC$_{l3}$ over a period of 5 mins at −70° C. The reaction mixture was allowed to warm to room temperature and was stirred for 1 hour.

In a third round bottom flask (50 ml), 5′-ODMTr-2′-OMOE-5-Me-uridine (930 mg, 1.5 mmol)[2] was co-evaporated three times with anhydrous toluene and was dissolved in THF (7.5 ml). Et$_3$N (2.1 ml, 15 mmol) was then added. The solution of 2-chloro-oxazaphospholidine intermediate was added via syringe over a period of 20 mins at −70° C. The reaction was allowed to warm up to room temperature and was stirred for 3 h. The reaction mixture was cooled to −20° C. and was quenched with saturated aqueous sodium bicarbonate solution (30 ml). The mixture was dilute with ethyl acetate (30 ml). The organic layer was separated and the aqueous layer was extracted twice with ethyl acetate (2×30 ml). The combined organic phases were washed with brine, dried over Na$_2$SO$_4$, filtered and concentrated. The crude material was passed through a very short of silica gel, which was flushed with elute (EA:hexane:Et$_3$N=80:20:2). The fractions containing the product were collected and concentrated to give the phosphoramidite Sp-6a as a white powder (1.10 g, 89%).

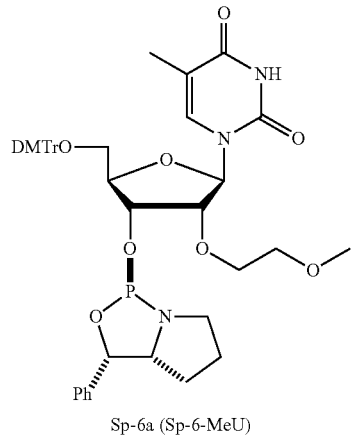

Sp-6a (Sp-6-MeU)

$^1$H NMR (400 MHz, CD$_3$CN) δ 9.06 (br s, 1 H), 7.54 (s, 1 H), 7.48-7.44 (m, 2 H), 7.36-7.21 (m, 12 H), 6.86 (dd, J=8.74, 0.89 Hz, 4 H), 5.86 (d, J=4.31 Hz, 1 H), 5.66 (d, J=6.59 Hz, 1 H), 4.80 (d, J=9.38 Hz, 1 H), 4.22-4.17 (m, 1 H), 4.15-4.09 (m, 1 H), 3.90 -3.82 (m, 1 H), 3.80-3.75 (m, 8 H), 3.69-3.65 (m, 1 H), 3.58-3.49 (m, 1 H), 3.47-3.43 (m, 2 H), 3.42 (d, J=2.28 Hz, 1 H), 3.28 (dd, J=11.15, 3.04 Hz, 2 H), 3.24 (s, 3 H), 3.11-3.01 (m, 2 H), 1.67-1.49 (m, 2 H), 1.21-1.13 (m, 1H), 0.90-0.85 (m, 1 H).

$^{31}$P NMR (161 MHz, CD$_3$CN) δ 151.63.

Synthesis of Sp-6b (Sp-6-iBuG)

Crude Sp-6b was synthesized from 5′-ODMTr-2′-OMOE-guanosine (715 mg, 1 mmol) and amino alcohol SR (355 mg, 2 mmol) following the procedure described above and purified by silica gel column chromatography (EA:Acetone:Et$_3$N=80:20:2) to give Sp-6b as a white powder (500 mg, 54%).

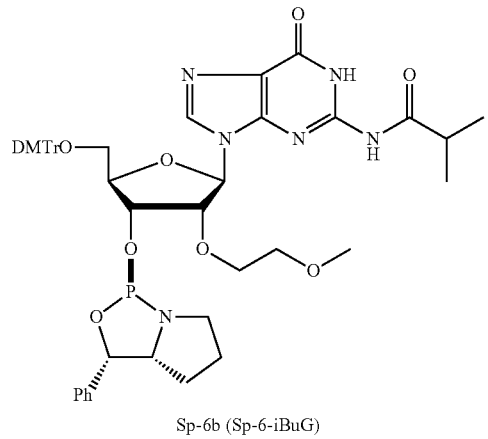

Sp-6b (Sp-6-iBuG)

$^1$H NMR (400 MHz, CD$_3$CN) δ 7.90 (s, 1 H), 7.49-7.42 (m, 2 H), 7.36-7.19 (m, 12 H), 6.83 (d, J=8.87 Hz, 4 H), 5.90 (d, J=5.58 Hz, 1 H), 5.62 (d, J=6.59 Hz, 1 H), 4.87 (dt, J=9.70, 4.66 Hz, 1 H), 4.68-4.61 (m, 1 H), 4.26-4.18 (m, 1 H), 3.85 (dt, J=13.31, 6.53 Hz, 1 H), 3.75 (s, 6 H), 3.73-3.69 (m, 2 H), 3.60-3.47 (m, 1 H), 3.45-3.39 (m, 3 H), 3.31 (dd, J=10.90, 4.31 Hz, 1 H), 3.19 (s, 3 H), 3.09-3.01(m, 1 H), 2.53-2.44 (m, 1 H), 1.65-1.49 (m, 2 H), 1.19-1.13 (m, 1 H), 1.13 (d, J=6.84 Hz, 3 H), 1.09 (d, J=6.84 Hz, 3 H), 0.93-0.83 (m, 1 H).

$^{31}$P NMR (161 MHz, CD$_3$CN) δ 151.28.

Synthesis of Sp-6c (Sp-6-AcC)

Crude Sp-6c was synthesized from 5'-ODMTr-2'-OMOE-Cytidine (645 mg, 1 mmol) and amino alcohol SR (355 mg, 2 mmol) following the procedure described above and purified by silica gel column chromatography (EA:Acetone: Et₃N=75:25:2) to give Sp-6c as a white powder (780 mg, 90%).

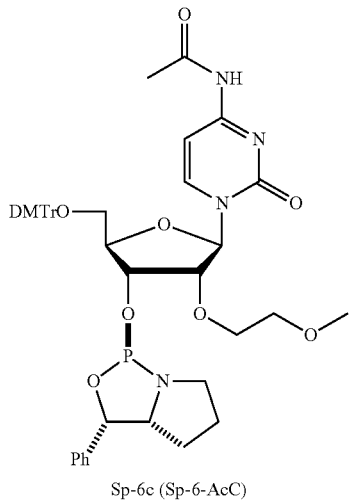

Sp-6c (Sp-6-AcC)

¹H NMR (400 MHz, CD₃CN) δ 8.86 (br.s, 1 H), 8.48 (d, J=7.35 Hz, 1 H), 7.50-7.46 (m, 2H), 7.40 -7.27 (m, 12 H), 7.02 (d, J=7.35 Hz, 1 H), 6.92-6.86 (m, 4 H), 5.87-5.82 (m, 2 H), 4.85-4.79 (m, 1 H), 4.20 (d,J=8.87 Hz, 1 H), 4.07-4.01 (m, 2 H), 3.91-3.85 (m, 1 H), 3.80 (s, 3 H), 3.79 (s, 3 H), 3.69 (ddd, J=10.96, 5.77, 3.55 Hz, 1 H), 3.64-3.56 (m, 1H), 3.54-3.42 (m, 4 H), 3.29 (s, 3 H), 3.18 -3.10 (m, 1 H), 2.15 (s, 3 H), 1.70-1.61 (m, 2

H), 1.19-1.11 (m, 1 H), 0.89 (dd, J=12.17, 8.87 Hz, 1 H).

³¹P NMR (161 MHz, CD₃CN) δ 154.13.

Synthesis of Sp-6d (Sp-6-BzMeC)

Crude Sp-6d was synthesized from 5'-ODMTr-2'-OMOE-5-Me-Cytidine (1.44 g, 2 mmol)² and amino alcohol SR (709 mg, 4 mmol) following the procedure described above and purified by silica gel column chromatography (EA: hexane:Et₃N=60:40:2) to give Sp-6d as a white powder (1.70 g, 91%).

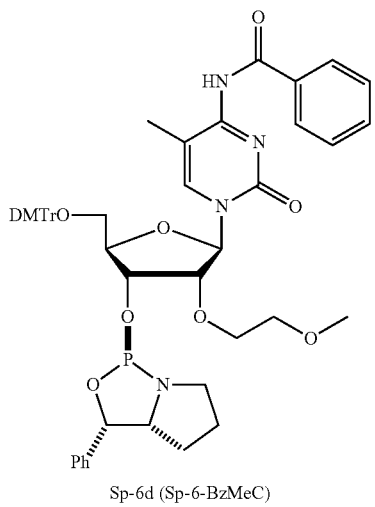

Sp-6d (Sp-6-BzMeC)

¹H NMR (400 MHz, CD₃CN) δ 13.25 (br s, 1 H), 8.23-8.33 (m, 2 H), 7.87 (d, J=1.01 Hz, 1 H), 7.62-7.53 (m, 1 H), 7.52-7.44 (m, 4 H), 7.38-7.25 (m, 12 H), 6.91-6.85 (m, 4 H), 5.89 (d, J=3.30 Hz, 1 H), 5.73 (d, J=6.59 Hz, 1 H), 4.93-4.81 (m, 1 H), 4.24 (dd, J =5.07, 3.55 Hz, 1 H), 4.22-4.16 (m, 1 H), 3.93-3.83 (m, 2 H), 3.77 (s, 6 H), 3.74-3.67 (m, 1

H), 3.61-3.44 (m, 4 H), 3.36 (dd, J=11.15, 3.04 Hz, 1 H), 3.26 (s, 3 H), 3.15-3.03 (m, 1 H), 1.51-1.70 (m, 5 H), 1.22-1.12 (m, 1 H), 0.94-0.84 (m, 1 H).

³¹P NMR (161 MHz, CD₃CN) δ 152.46.

Synthesis of Sp-6e (Sp-6-BzA)

Crude Sp-6e was synthesized from 5'-ODMTr-2'-OMOE-Adenosine (732 mg, 1 mmol) and amino alcohol SR (355 mg, 2 mmol) following the procedure described above and purified by silica gel column chromatography (EA: Et₃N=100:2) to give Sp-6e as a white powder (700 mg, 78%).

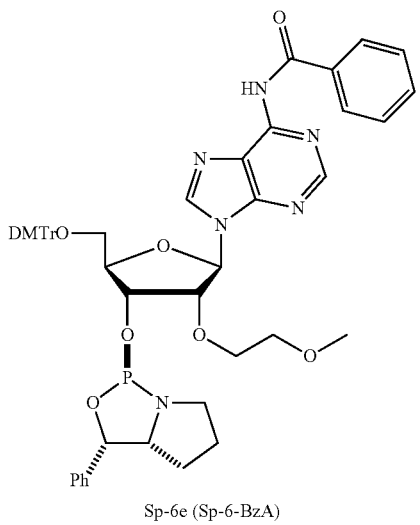

Sp-6e (Sp-6-BzA)

¹H NMR (400 MHz, CD₃CN) δ 9.32 (br s, 1 H), 8.68 (s, 1 H), 8.35 (s, 1 H), 8.03 (d, J=7.60 Hz, 2 H), 7.66 (d, J=7.60 Hz, 1 H), 7.62-7.53 (m, 2 H), 7.44-7.18 (m, 14 H), 6.86 -6.73 (m, 4 H), 6.14 (d, J=4.31 Hz, 1 H), 5.82 (d, J=6.59 Hz, 1 H), 5.25-5.14 (m, 1 H), 4.94 (t, J=4.56 Hz, 1 H), 4.26 (d, J=5.32 Hz, 1 H), 4.04-3.94 (m, 1 H), 3.83-3.69 (m, 7 H), 3.65-3.44 (m, 4 H), 3.30 (dd, J=10.90, 4.06 Hz, 1 H), 3.21 (s, 3 H), 3.12 (dd, J=8.11, 5.58 Hz, 1 H), 1.72-1.51 (m, 2 H), 1.26-1.16 (m, 2 H), 0.91 (dd, J=12.42, 8.36 Hz, 1 H).

³¹P NMR (161 MHz, CD₃CN) δ 150.21.

Synthesis of Sp-6f (Sp-6-U)

Crude Sp-6f was synthesized from 5'-ODMTr-2'-OMOE-Uridine (605 mg, 1 mmol) and amino alcohol 5R (355 mg, 2 mmol) following the procedure described above and purified by silica gel column chromatography (EA:hexane: Et₃N=75:25:2) to give Sp-6f as a white powder (689 mg, 85%).

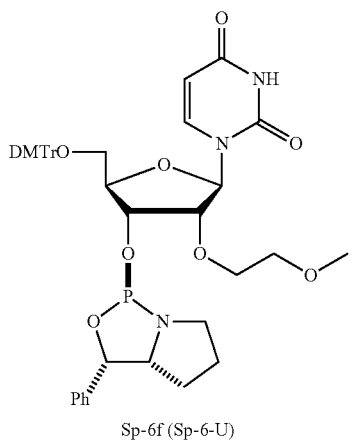

Sp-6f (Sp-6-U)

¹H NMR (400 MHz, CD₃CN) δ 9.02 (br s, 1 H), 7.85 (d, J=8.11 Hz, 1 H), 7.52-7.44 (m, 2 H), 7.43-7.24 (m, 12 H), 6.93-6.85 (m, 4 H), 5.83 (d, J=3.04 Hz, 1 H), 5.79 (d, J =6.34 Hz, 1 H), 5.30 (d, J=8.11 Hz, 1 H), 4.84-4.76 (m, 1 H), 4.17-4.11 (m, 2 H), 3.95 -3.88 (m, 1 H), 3.85-3.80 (m, 1 H), 3.79 (s, 6 H), 3.72-3.65 (m, 1 H), 3.63-3.54 (m, 1 H), 3.50-3.45 (m, 3 H), 3.42-3.37 (m, 1 H), 3.28 (s, 3 H), 3.18-3.07 (m, 1 H), 1.72 -1.52 (m, 2 H), 1.21-1.14 (m, 1 H), 0.96-0.86 (m, 1H).

³¹P NMR (161 MHz, CD₃CN) δ 152.65.

Synthesis of Rp-6a (Rp-6-MeU)

Crude Rp-6a was synthesized from 5'-ODMTr-2'-OMOE-5-Me-Uridine (930 mg, 1.5 mmol)² and amino alcohol 5L (535 mg, 3 mmol) following the procedure described above and purified by silica gel column chromatography (EA:hexane:Et₃N=80:20:2) to give Rp-6a as a white powder (810 mg, 68%).

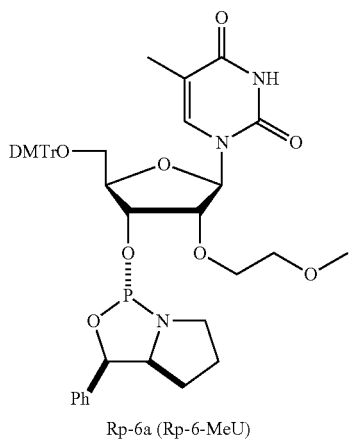

Rp-6a (Rp-6-MeU)

¹H NMR (400 MHz, CD₃CN) δ 8 8.99 (br s, 1 H), 7.52-7.41 (m, 2 H), 7.40-7.20 (m, 13 H), 6.85 (dd, J=8.87, 1.77 Hz, 4 H), 5.89 (d, J=3.60 Hz, 1 H), 5.77 (d, J=6.70 Hz, 1 H), 4.71-4.76 (m, 1 H), 4.24-4.21 (m, 1 H), 4.14-4.12 (m, 1 H), 3.83-3.74 (m, 9 H), 3.56-3.45 (m, 3 H), 3.41-3.35 (m, 1 H), 3.31-3.27 (m, 4 H), 3.04-2.96 (m, 1 H), 1.61-1.50 (m, 2 H), 1.42 (d, J=1.01 Hz, 3 H), 1.18-1.09 (m, 1 H), 0.91-0.83 (m, 1 H).

³¹P NMR (161 MHz, CD₃CN) δ 152.95.

Synthesis of Rp-6b (Rp-6-iBuG)

Crude Rp-6b was synthesized from 5'-ODMTr-2'-OMOE-guanosine (715 mg, 1 mmol) and amino alcohol 5L (355 mg, 2 mmol) following the procedure described above and purified by silica gel column chromatography (EA:Acetone:Et₃N=80:20:2) to give Rp-6b as a white powder (600 mg, 65%).

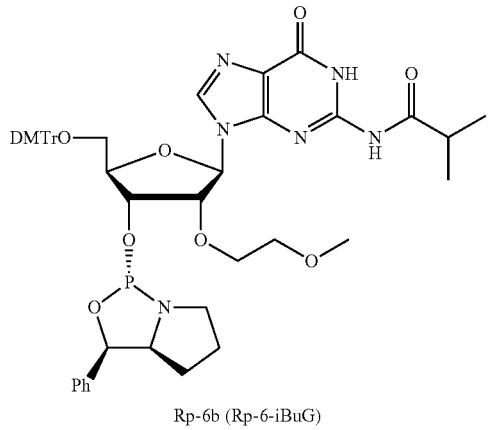

Rp-6b (Rp-6-iBuG)

¹H NMR (400 MHz, CD₃CN) δ 7.86 (s, 1 H), 7.45-7.15 (m, 14 H), 6.81 (dd, J=9.00, 2.41 Hz, 4 H), 5.89 (d, J=6.08 Hz, 1 H), 5.76 (d, J=6.34 Hz, 1 H), 4.78 (dd, J=9.76, 3.93 Hz, 1 H), 4.71-4.68 (m, 1 H), 4.22 (d, J=3.80 Hz, 1 H), 3.80-3.65 (m, 10 H), 3.49-3.44 (m, 3H), 3.35-3.33 (m, 1 H), 3.26-3.23 (m, 1 H), 3.21 (s, 3 H), 3.15-3.08 (m, 1 H), 2.55-2.49 (m, 1 H), 1.60-1.50 (m, 2 H), 1.18-1.05 (m, 7 H), 0.90-0.84 (m, 1H).

³¹P NMR (161 MHz, CD₃CN) δ 153.47.

Synthesis of Rp-6c (Rp-6-AcC)

Crude Rp-6c was synthesized from 5'-ODMTr-2'-OMOE-Cytidine (645 mg, 1 mmol) and amino alcohol 5L (355 mg, 2 mmol) following the procedure described above and purified by silica gel column chromatography (EA:Acetone:Et₃N=75:25:2) to give Rp-6c as a white powder (440 mg, 54%).

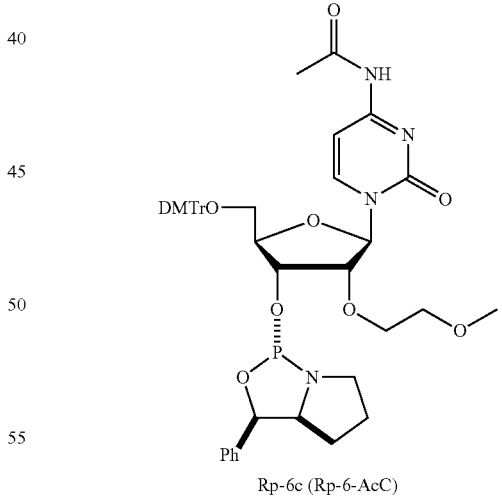

Rp-6c (Rp-6-AcC)

¹H NMR (400 MHz, CD₃CN) δ 8.81 (br s, 1 H), 8.33 (d, J=7.60 Hz, 1 H), 7.19-7.46 (m, 14 H), 6.95 (d, J=7.60 Hz, 1 H), 6.84 (dd, J=8.87, 2.53 Hz, 4 H), 5.85 (d, J=1.01 Hz, 1 H), 5.75 (d, J=6.59 Hz, 1 H), 4.77 (td, J=8.43, 4.94 Hz, 1 H), 4.22-4.14 (m, 1 H), 4.11 -4.07 (m, 1 H), 4.01-3.93 (m, 1 H), 3.93-3.88 (m, 1 H), 3.87-3.82 (m, 1 H), 3.74 (s, 3 H), 3.73 (s, 3 H), 3.56-3.49 (m, 3 H), 3.46 (d, J=2.53 Hz, 2 H), 3.30 (s, 3 H), 3.05-2.96 (m, 1 H), 2.12 (s, 3 H), 1.67-1.44 (m, 2 H), 1.22-1.13 (m, 1 H), 0.96-0.86 (m, 1 H).

³¹P NMR (161 MHz, CD₃CN) δ 153.87.

Synthesis of Rp-6d (Rp-6-BzMeC)

Crude Rp-6d was synthesized from 5'-ODMTr-2'-OMOE-5-Me-Cytidine (1.44 g, 2 mmol) and amino alcohol SL (709 mg, 4 mmol) following the procedure described above and purified by silica gel column chromatography (EA:hexane: Et$_3$N=60:40:2) to give Rp-6d as a white powder (1.30 g, 70%).

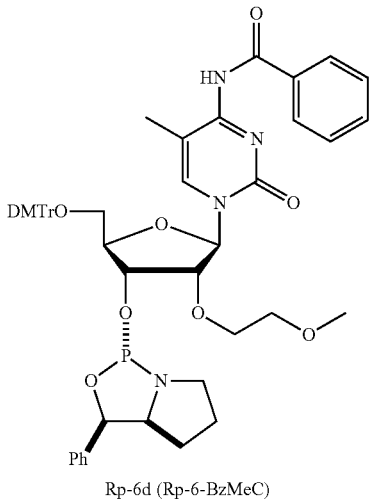

Rp-6d (Rp-6-BzMeC)

$^1$H NMR (400 MHz, CD$_3$CN) δ 13.09 (br s, 1 H), 8.28-8.26 (m, 2 H), 7.79 (d, J=1.01 Hz, 1 H), 7.59-7.55 (m, 1 H), 7.50-7.45 (m, 4 H), 7.41-7.23 (m, 12 H), 6.89-6.84 (m, 4 H), 5.93 (d, J=4.31 Hz, 1 H), 5.78 (d, J=6.34 Hz, 1 H), 4.81-4.76 (m, 1 H), 4.27 (t, J=4.82 Hz, 1 H), 4.20-4.18 (m, 1 H), 3.88-3.81 (m, 3 H), 3.77-3.74 (m, 7 H), 3.57-3.47 (m, 2 H), 3.45-3.42 (m, 1 H), 3.37-3.34 (m, 1 H), 3.28 (s, 3 H), 3.06-2.96 (m, 1 H), 1.62 (d, J=1.01 Hz, 3 H), 1.60-1.48 (m, 2 H), 1.20-1.12 (m, 1 H), 0.93-0.84 (m, 1 H).

$^{31}$P NMR (161 MHz, CD$_3$CN) δ 153.03.

Synthesis of Rp-6e (Rp-6-BzA)

Crude Rp-6e was synthesized from 5'-ODMTr-2'-OMOE-Adenosine (732 mg, 1 mmol) and amino alcohol SL (355 mg, 2 mmol) following the procedure described above and purified by silica gel column chromatography (EA:Et$_3$N=100:2) to give Rp-6e as a white powder (500 mg, 64%).

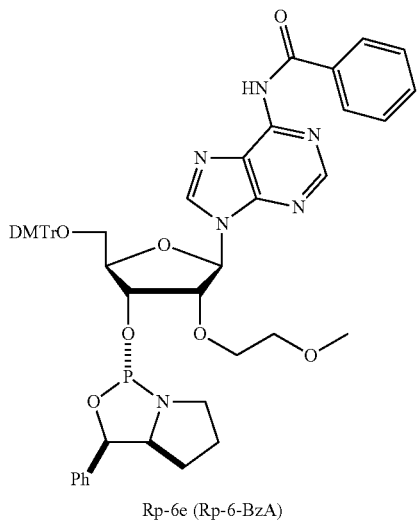

Rp-6e (Rp-6-BzA)

$^1$H NMR (400 MHz, CD$_3$CN) δ 9.26 (br s, 1 H), 8.63 (s, 1 H), 8.29 (s, 1 H), 8.00 (d, J=7.35 Hz, 2 H), 7.64 (d, J=7.35 Hz, 1 H), 7.60-7.52 (m, 2 H), 7.44-7.34 (m, 4 H), 7.33-7.17 (m, 10 H), 6.78 (dd, J=8.87, 2.28 Hz, 4 H), 6.09 (d, J=4.56 Hz, 1 H), 5.88 (d, J=6.34 Hz, 1 H), 5.14-5.08 (m, 1 H), 4.88 (t, J=4.82 Hz, 1 H), 4.25 (d, J=4.31 Hz, 1 H), 4.00-3.90 (m, 1 H), 3.85-3.77 (m, 1 H), 3.76-3.64 (m, 7 H), 3.58-3.48 (m, 1 H), 3.46-3.44 (m, 2 H), 3.41 (d, J=3.80 Hz, 1 H), 3.31 (dd, J=10.65, 4.82 Hz, 1 H), 3.19 (s, 3 H), 3.02-2.92 (m, 1 H), 1.68-1.49 (m, 2 H), 1.22-1.12 (m, 1 H), 0.94-0.85 (m, 1 H).

$^{31}$P NMR (161 MHz, CD$_3$CN) δ 151.88.

Synthesis of Rp-6f (Rp-6-U)

Crude Rp-6f was synthesized from 5'-ODMTr-2'-OMOE-Uridine (605 mg, 1 mmol) and amino alcohol 5L (355 mg, 2 mmol) following the procedure described above and purified by silica gel column chromatography (EA:hexane: Et$_3$N=75:25:2) to give Rp-6f as a white powder (400 mg, 49%).

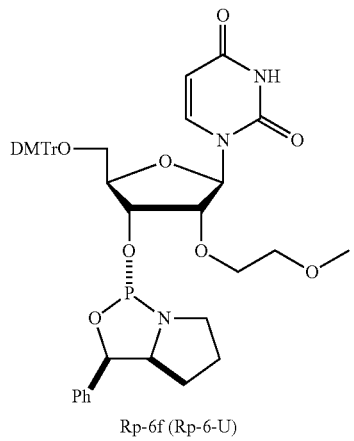

Rp-6f (Rp-6-U)

H NMR $^1$H NMR (400 MHz, CD$_3$CN) δ 9.03 (br s, 1 H), 7.74 (d, J=8.11 Hz, 1 H), 7.48-7.37 (m, 4 H), 7.36-7.24 (m, 10 H), 6.91-6.84 (m, 4 H), 5.86 (d, J=3.80 Hz, 1 H), 5.82 (d, J=6.59 Hz, 1 H), 5.31 (d, J=8.11 Hz, 1 H), 4.76 (dt, J=9.25, 5.51 Hz, 1 H), 4.18-4.12 (m, 2 H), 3.96-3.87 (m, 1 H), 3.83-3.75 (m, 8 H), 3.61-3.50 (m, 3 H), 3.41 (d, J=3.04 Hz, 2 H), 3.31 (s, 3 H), 3.09-2.99 (m, 1 H), 1.69-1.48 (m, 2 H), 1.24-1.15 (m, 1 H), 0.99-0.87 (m, 1 H).

$^{31}$H NMR (161 MHz, CD$_3$CN) δ 153.33

Example 3

Synthesis of Chirally Uniform MOE-Oligoribonucleotides

Oligoribonucleotides were prepared on MerMade 192 DNA/RNA synthesizer using CPG 500 A unylinker support (44.9 μmol/g). Fully protected stereopure nucleoside phosphoramidites were incorporated using standard solid-phase oligonucleotide synthesis conditions: i.e. 3% dichloroacetic acid in dichloromethane (DCM) for deblocking, 1.4 M N-phenyl imidazolium triflate in anhydrous acetonitrile as activator, capping reagent A (THF/lutidine/acetic anhydride, 8:1:1) and capping reagent B (16% N-imidazole/THF) for capping, a 0.05 M solution of 3-((N,N-dimethylaminomethylidene)amino)-3H-1,2,4-dithia-zole-5-thione (DDTT; Sulfurizing Reagent II; Glen Research, Virginia) in dry pyridine/ACN (60:40) for sulfurization. ORN amidites were prepared at 0.11 M in anhydrous acetonitrile and were coupled utilizing three application of ORN amidites, with a 4 min contact time for each pass. After the completion of the synthesis, the solid support was suspended in aqueous ammonia (25%, 300 µl) and heated at 55° C. for 24 hours. The reaction was cooled down to room temperature, and the solid support was filtered and washed with 400 µl of EtOH and H$_2$O 1:1 (v/v). The filtrate was concentrated to dryness and the residue was dissolved in 200 µl water.

RP-HPLC purification of Oligoribonucleotides

The oligonucleotides were purified on an Agilent 1200 series preparative HPLC fitted with a WatersXBridge OST C-18 column, 10×50 mm, 2.5 µm, at 65° C.).

Running buffer for HPLC purification of single-stranded ORNs: buffer A (0.1 M triethylammonium acetate), buffer B (methanol); gradient for the DMT-on purification: 5-80% buffer B over 6 min; gradient for the DMT-off purification: 5-35% buffer B over 5 min. Fractions containing the product were collected and dried in a miVac duo SpeedVac from Genevac. The oligonucleotides were analysed by LC-MS (Agilent 1200/6130 system) on a Waters Acquity OST C-18 column, 2.1 × 50 mm, 1.7 µm, 65° C. Buffer A: 0.4 M HFIP, 15 mM triethylamine; buffer B: MeOH. Gradient: 10-50% B in 20 min; flow rate: 0.3 ml min$^{-1}$.

All-(Rp)-PS-mUAGmCAGmCmCmUGAG (SEQ ID NO:1) was synthesized following the procedure described above.

Isolated yield 1.8%, which was determined by UV quantitation at 260 nm, LC-MS: 4777.44 (DMT off).

Furthermore, all-(Sp)-PS-mUAGmCAGmCmCmUGAG (SEQ ID NO:2) was synthesized following the procedure described above.

Isolated yield 1.1%, which was determined by UV quantitation at 260 nm, LC-MS: 4776.18 (DMT off).

The invention claimed is:

1. A compound of formula (Ia) or formula (Ib),

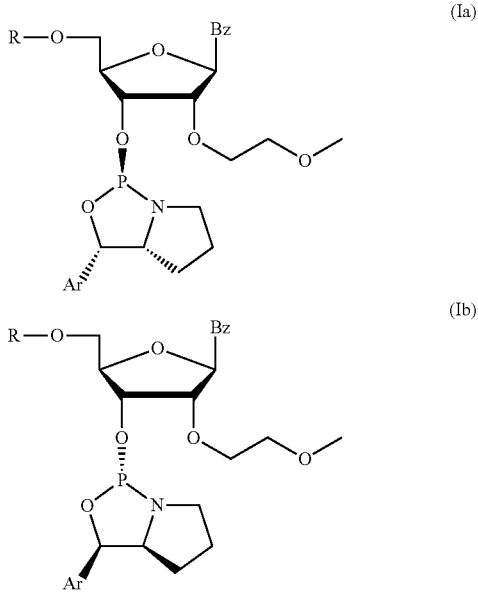

wherein Ar is phenyl (Ph, $C_6H_5$) optionally substituted with: halogen, $C_1$-$C_6$alkyl, $C_3$-$C_6$cycloalkyl, or $C_1$-$C_4$alkoxy; and R is a protective group of a hydroxyl group; and Bn is selected from (i) adenine, (ii) cytosine, (iii) 5-methylcytosine, (iv) guanine, (v) uracil, (vi) 5-methyluracil, or (vii) a derivative of (i), (ii), (iii), (iv), (v) or (vi).

2. The compound of formula (Ia) or formula (Ib) of claim 1, wherein Ar is phenyl optionally substituted with halogen, $C_1$-$C_6$alkyl, $C_3$-$C_6$cycloalkyl, $C_1$-$C_4$alkoxy.

3. The compound of formula (Ia) or formula (Ib) of claim 1, wherein Ar is phenyl.

4. The compound of formula (Ia) or formula (Ib) of claim 1, wherein said R is selected from triphenylmethyl (trityl), 4-monomethoxytrityl (MMTr), 4,4'-dimethoxytrityl (DMTr), 4,4 ', 4 "-trimethoxytrityl, 9-phenylxanthin-9-yl (Pixyl) and 9-(p-methoxyphenyl)xanthin-9-yl (MOX).

5. The compound of formula (Ia) or formula (Ib) of claim 1, wherein said derivative is derived from said adenine, cytosine, 5-methylcytosine or said guanine, wherein the exocyclic amino group of said adenine, cytosine, 5-methylcytosine or said guanine is protected by a protecting group.

6. The compound of formula (Ia) or formula (Ib) of claim 5, wherein said protecting group is independently of each other selected from —C(O)-$R^1$, wherein independently of each other $R^1$ is selected from $C_1$-$C_{10}$alkyl, $C_6$-$C_{10}$aryl$C_6$-$C_{10}$aryl$C_1$-$C_{10}$alkylene, or $C_6$-$C_{10}$aryloxy$C_1$-$C_{10}$alkylene or from a dialkylformamidino protecting group is =C(H)-N$R^2R^3$, wherein $R^2$ and $R^3$ are independently of each other selected from $C_1$-$C_4$alkyl.

7. The compound of formula (Ia) or formula (Ib) of claim 5, wherein said protecting group is independently of each other selected from —C(O)-$R^1$, wherein independently of each other $R^1$ is selected from $C_1$-$C_3$alkyl; phenyl; phenyl substituted with $C_1$-$C_3$alkyl, methoxy; benzyl; benzyl substituted with $C_1$-$C_3$alkyl, methoxy; or phenyloxymethylene ($CH_2$-$OC_6H_5$) wherein the $C_6H_5$ is optionally substituted with $C_1$-$C_3$alkyl, methoxy; or from a dialkylformamidino protecting group, wherein said dialkylformamidino protecting group is dimethylformamidino (DMF).

8. The compound of formula (Ia) or formula (Ib) of claim 5, wherein said protecting group is independently of each other selected from —C(O)-$R^1$, wherein independently of each other $R^1$ is selected from methyl, iso-propyl, phenyl, $CH_2$-$OC_6H_5$ wherein the $C_6H_5$ is optionally substituted with iso-propyl; or from a dialkylformamidino protecting group, wherein said dialkylformamidino protecting group is dimethylformamidino (DMF).

9. The compound of formula (Ia) or formula (Ib) of claim 1, wherein the compound is represented by formula Sp-6a, Sp-6b, Sp-6c, Sp-6d, Sp-6e, Sp-6f, Rp-6a, Rp-6b, Rp-6c, Rp-6d, Rp-6e, or Rp-6f

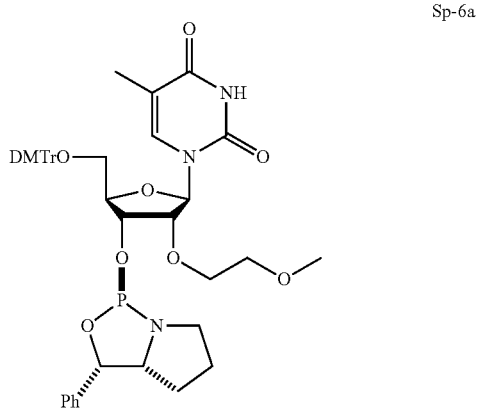

Sp-6a

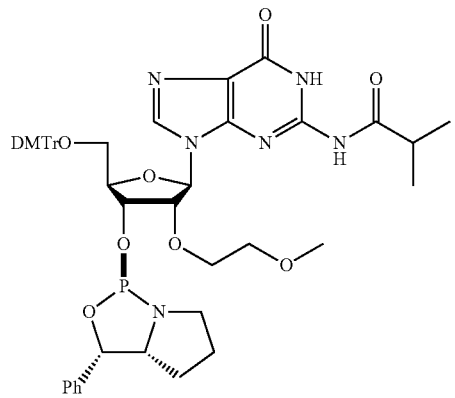
Sp-6b
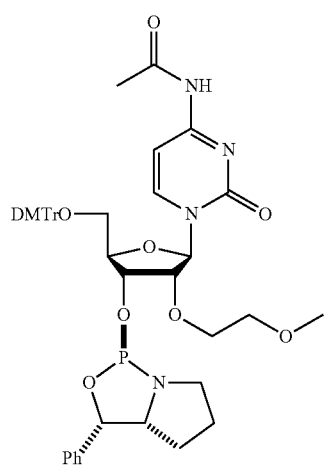
Sp-6c
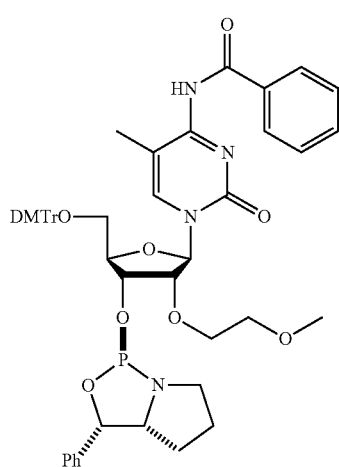
Sp-6d
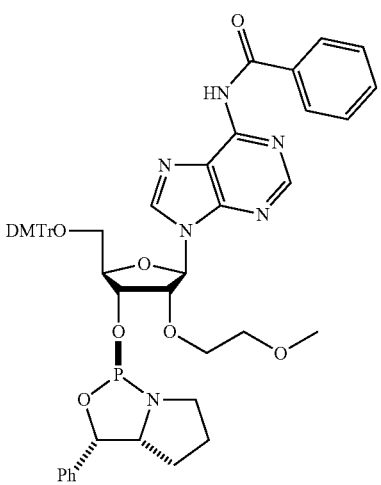
Sp-6e
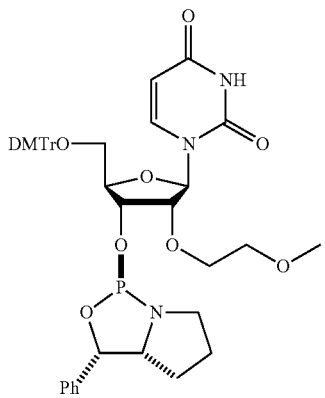
Sp-6f
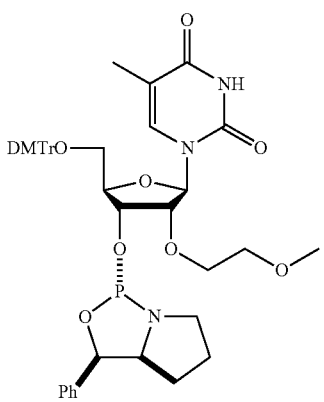
Rp-6a -continued

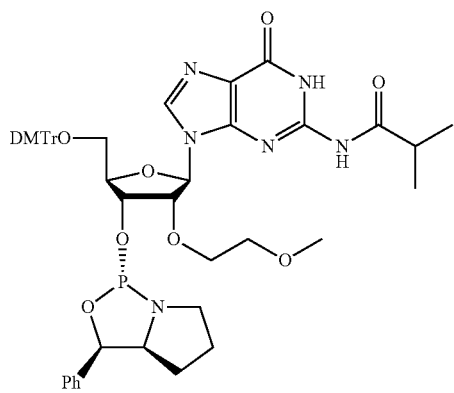
Rp-6b

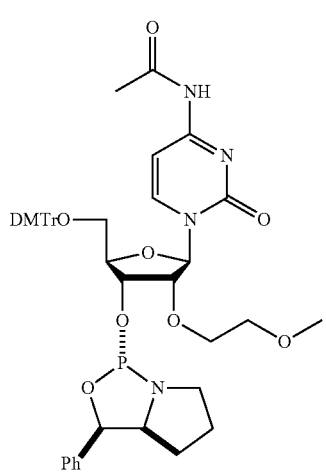
Rp-6c

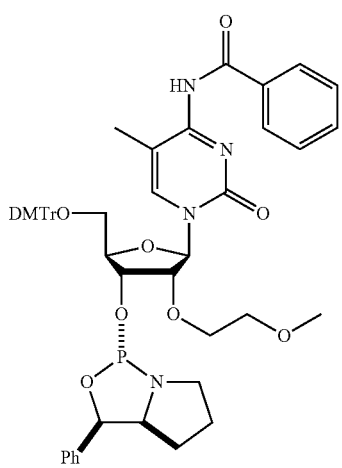
Rp-6d

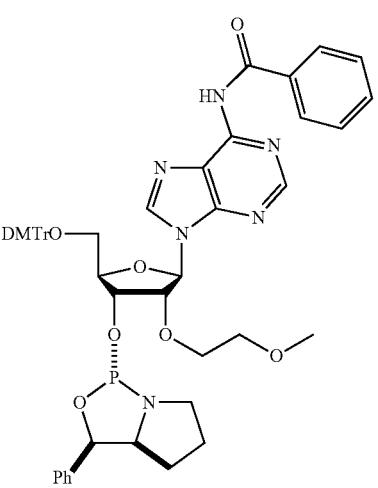
Rp-6e

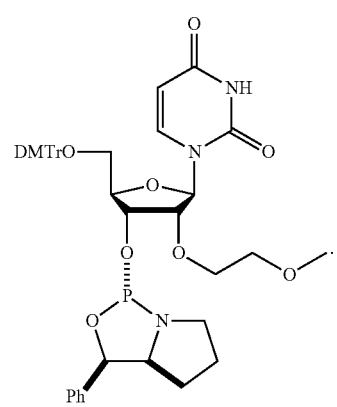
Rp-6f

10. The compound of formula (Ia) or formula (Ib) of claim 1, wherein said R is 4,4'-dimethoxytrityl (DMTr) or 4-monomethoxytrityl (MMTr).

11. The compound of formula (Ia) or formula (Ib) of claim 5, wherein said protecting group is an acyl protecting group or dialkylformamidino.

12. The compound of formula (Ia) or formula (Ib) of claim 5, wherein said protecting group is dimethylformamidino (DMF).

13. The compound of formula (Ia) or formula (Ib) of claim 5, wherein Ar is phenyl.

14. The compound of formula (Ia) or formula (Ib) of claim 13, wherein said R is selected from triphenylmethyl (trityl), 4-monomethoxytrityl (MMTr), 4,4'-dimethoxytrityl (DMTr), 4,4',4''-trimethoxytrityl, 9-phenylxanthin-9-yl (Pixyl) and 9-(p-methoxyphenyl)xanthin-9-yl (MOX).

15. The compound of formula (Ia) or formula (Ib) of claim 14, wherein said R is 4,4'-dimethoxytrityl (DMTr) or 4-monomethoxytrityl (MMTr).

16. The compound of formula (Ia) or formula (Ib) of claim 6, wherein Ar is phenyl.

17. The compound of formula (Ia) or formula (Ib) of claim 16, wherein said R is selected from triphenylmethyl (trityl), 4-monomethoxytrityl (MMTr), 4,4'-dimethoxytrityl (DMTr), 4,4',4''-trimethoxytrityl, 9-phenylxanthin-9-yl (Pixyl) and 9-(p-methoxyphenyl)xanthin-9-yl (MOX).

18. The compound of formula (Ia) or formula (Ib) of claim 17, wherein said R is 4,4'-dimethoxytrityl (DMTr) or 4-monomethoxytrityl (MMTr).

19. The compound of formula (Ia) or formula (Ib) of claim 7, wherein Ar is phenyl.

20. The compound of formula (Ia) or formula (Ib) of claim 19, wherein said R is selected from triphenylmethyl (trityl), 4-monomethoxytrityl (MMTr), 4,4'-dimethoxytrityl (DMTr), 4,4',4''-trimethoxytrityl, 9-phenylxanthin-9-yl (Pixyl) and 9-(p-methoxyphenyl)xanthin-9-yl (MOX).

21. The compound of formula (Ia) or formula (Ib) of claim 20, wherein said R is 4,4'-dimethoxytrityl (DMTr) or 4-monomethoxytrityl (MMTr).

22. The compound of formula (Ia) or formula (Ib) of claim 8, wherein Ar is phenyl.

23. The compound of formula (Ia) or formula (Ib) of claim 22, wherein said R is selected from triphenylmethyl (trityl), 4-monomethoxytrityl (MMTr), 4,4'-dimethoxytrityl (DMTr), 4,4',4''-trimethoxytrityl, 9-phenylxanthin-9-yl (Pixyl) and 9-(p-methoxyphenyl)xanthin-9-yl (MOX).

24. The compound of formula (Ia) or formula (Ib) of claim 23, wherein said R is 4,4'-dimethoxytrityl (DMTr) or 4-monomethoxytrityl (MMTr).

25. A method for synthesizing a stereodefined phosphorothioate MOE oligonucleotide comprising the step of coupling a compound of formula (Ia) or formula (Ib) of claim 1 to either an oligonucleotide synthesis support or a preceding nucleotide, wherein said stereodefined phosphorothioate MOE oligonucleotide comprises at least one stereospecific phosphorothioate nucleotide pair wherein the internucleoside linkage between the nucleosides of the at least one stereospecific phosphorothioate nucleotide pair is either in the Sp configuration or in the Rp configuration, and wherein at least one of the nucleosides of the at least one stereospecific phosphorothioate nucleotide pair is a MOE nucleoside.

26. The method of claim 25, wherein said phosphorothioate MOE oligonucleotide is chirally pure.

27. The method of claim 25, wherein said phosphorothioate MOE oligonucleotide is chirally uniform.

28. The method of claim 25, wherein said MOE oligonucleotide is comprised by a gapmer oligonucleotide.

29. The method of claim 28, wherein each wing of said gapmer comprises said MOE oligonucleotide, and wherein each wing of said gapmer comprises one or more stereospecific phosphorothioate internucleoside linkage between at least two adjacent MOE nucleosides comprised by said MOE oligonucleotide.

30. The method of claim 25, wherein said method comprises said coupling step, and further comprises the steps of capping, sulfurization, deprotecting, and repeating said steps until a desired length of said MOE oligonucleotide is achieved.

\* \* \* \* \*